(12) United States Patent
Fischer et al.

(10) Patent No.: US 9,206,122 B2
(45) Date of Patent: Dec. 8, 2015

(54) PESTICIDAL ARYLPYRROLIDINES

(71) Applicant: BAYER INTELLECTUAL PROPERTY GMBH, Monheim (DE)

(72) Inventors: Reiner Fischer, Monheim (DE); Peter Bruechner, Krefeld (DE); Tobias Kapferer, Cologne (DE); Kerstin Ilg, Cologne (DE); Ulrich Goergens, Ratingen (DE); Arnd Voerste, Cologne (DE); Mamoru Hatazawa, Ibaraki (JP); Eiichi Shimojo, Tochigi (JP)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/384,840

(22) PCT Filed: Mar. 12, 2013

(86) PCT No.: PCT/EP2013/055042
§ 371 (c)(1),
(2) Date: Sep. 12, 2014

(87) PCT Pub. No.: WO2013/135724
PCT Pub. Date: Sep. 19, 2013

(65) Prior Publication Data
US 2015/0025253 A1      Jan. 22, 2015

(30) Foreign Application Priority Data
Mar. 14, 2012   (EP) ..................................... 12159494

(51) Int. Cl.
*C07D 207/12*   (2006.01)
*C07D 401/04*   (2006.01)

(52) U.S. Cl.
CPC ............ *C07D 207/12* (2013.01); *C07D 401/04* (2013.01)

(58) Field of Classification Search
CPC .................................................... C07D 207/12
See application file for complete search history.

(56) References Cited

U.S. PATENT DOCUMENTS

| | | |
|---|---|---|
| 8,188,122 B2 | 5/2012 | Mihara et al. |
| 8,450,483 B2 | 5/2013 | Gorgens et al. |
| 8,536,201 B2 | 9/2013 | Mihara et al. |
| 8,785,647 B2 | 7/2014 | Gorgens et al. |
| 2014/0046069 A1 | 2/2014 | Mihara et al. |

FOREIGN PATENT DOCUMENTS

| | | |
|---|---|---|
| JP | 2008110971 A | 5/2008 |
| WO | 2008128711 A1 | 10/2008 |
| WO | 2011080211 A1 | 12/2009 |
| WO | 2010043315 A1 | 4/2010 |
| WO | 2012035011 A1 | 3/2012 |

OTHER PUBLICATIONS

International Search Report received in PCT/EP2013/055042, mailed Apr. 12, 2013.

*Primary Examiner* — Rebecca Anderson
*Assistant Examiner* — Karen Cheng
(74) *Attorney, Agent, or Firm* — Miles & Stockbridge P.C.

(57) ABSTRACT

Arylpyrrolidines of formula (I):

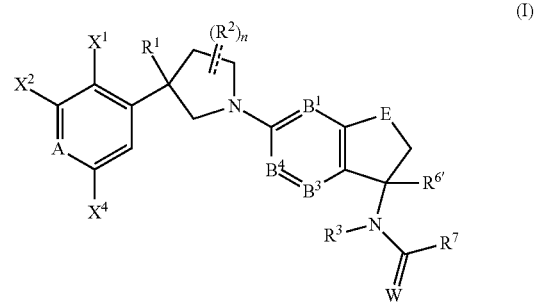

wherein each substituent is as defined in the specification, and use thereof as pesticides and animal parasite-controlling agents.

13 Claims, No Drawings

PESTICIDAL ARYLPYRROLIDINES

CROSS REFERENCE TO RELATED APPLICATIONS

This application is a §371 National Stage Application of PCT/EP2013/055042, filed Mar. 12, 2013, which claims priority to EP 12159494.9, filed Mar. 14, 2012.

BACKGROUND

1. Field of the Invention

The present invention relates to novel arylpyrrolidines and use thereof as pesticides.

2. Description of Related Art

Several arylpyrrolidine compounds have been described in WO 2008/128711, WO 2010/043315 and WO 2011/080211 which can be used as pest-controlling agents. Moreover, from JP 2008-110971 several nitrogen-containing heterocyclic compounds are known to be useful as pest-controlling agents. Aryl-hydroxypyrrolidine compounds are known from WO 2012/035011.

Since ecological and economic demands on modern plant treatment agents are continually increasing, particularly in respect to the amount applied, residue formation, selectivity, toxicity and favourable production methodology, and also because, for example, resistance problems can occur, there is the on-going task to develop new plant treatment agents that at least in certain areas are able to demonstrate advantages over known agents.

Inventors of the present invention extensively studied to develop novel compounds which are highly effective as pesticides and have a broad spectrum of use. As a result, the inventors found that the novel compounds represented by formula (I) have a high activity, a broad spectrum of use and safety, and also are effective against pests that are resistant to an organic phosphorous agent or a carbamate agent.

SUMMARY

Thus, this invention is directed to compounds of formula (I):

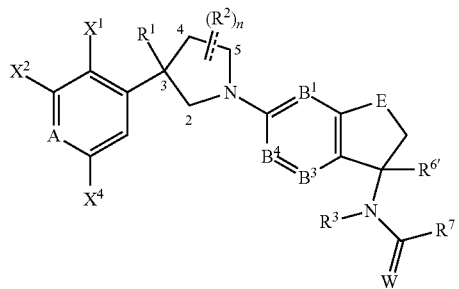

wherein
the dotted line stands for a bond, or has no meaning, which means that $R^2$ can be bound via a double or a single bond to the pyrrolidine ring;
if the dotted line stands for a bond, so that $R^2$ is bound through a double bond to the pyrrolidine ring, then $R^2$ is oxo and/or thioxo and n is 1 or 2; preferably $R^2$ is oxo and n is 1; more preferably $R^2$ is 2-oxo or 5-oxo;
if the dotted line has no meaning, so that $R^2$ is bound through a single bond to the pyrrolidine ring, then $R^2$ independently is halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, sulfur pentafluoride, $C_{1-12}$ alkoxy-carbonyl, $C_{1-12}$ haloalkoxy-carbonyl, $C_{1-12}$ alkoxy-carbonyloxy or $C_{1-12}$ haloalkoxy-carbonyloxy; preferably $R^2$ is hydroxy, chloro, bromo or iodo and n is 1 or 2; more preferably $R^2$ is hydroxy and n is 1 or 2, most preferably $R^2$ is hydroxy and n is 1; in particular $R^2$ is 2-hydroxy, or 5-hydroxy;

$R^1$ is $C_{1-12}$ alkyl, $C_{3-8}$ cycloalkyl, $C_{1-12}$ haloalkyl, $C_{3-8}$ halocycloalkyl; $R^1$ is preferably $C_{1-4}$ haloalkyl; more preferably $R^1$ is $CF_3$;

A is C—$X^3$ or nitrogen;

$X^1$, $X^2$, $X^3$ and $X^4$ each independently are hydrogen, halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino or sulfur pentafluoride; preferably $X^1$, $X^2$, $X^3$ and $X^4$ each independently are hydrogen, fluoro, chloro, bromo or iodo or $C_{1-4}$ haloalkyl; more preferably $X^1$, $X^2$, $X^3$ and $X^4$ each independently are hydrogen, fluoro, chloro, bromo or trifluoromethyl;

$B^1$ is C—$Y^1$ or nitrogen; $B^1$ preferably is C—H, C—F or nitrogen;

$B^3$ is C—$Y^3$ or nitrogen; $B^3$ preferably is C—H;

$B^4$ is C—$Y^4$ or nitrogen; $B^4$ preferably is C—H, or C—F or nitrogen; or $Y^1$, $Y^3$, and $Y^4$ each independently are hydrogen, halogen, nitro, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino, sulfur pentafluoride, aryl or heterocyclyl;

$Y^1$, $Y^3$, and $Y^4$ each independently are preferably hydrogen, halogen, $C_{1-4}$ alkyl, $C_{1-4}$ haloalkyl, $C_{1-4}$ haloalkoxy, phenyl, pyridyl, $C_{1-4}$ alkoxy, cyano, cyclopropyl; more preferably $Y^1$ is hydrogen or fluoro and/or $Y^3$ is hydrogen and/or $Y^4$ is hydrogen, fluoro; or $R^3$ is hydrogen, cyano, hydroxy, mercapto, amino, $C_{1-12}$ alkyl, $C_{1-12}$ haloalkyl, $C_{2-12}$ alkenyl, $C_{2-12}$ haloalkenyl, $C_{2-12}$ alkynyl, $C_{2-12}$ haloalkynyl, $C_{1-12}$ alkyl-carbonyl, $C_{1-12}$ haloalkyl-carbonyl, $C_{1-12}$ alkoxy-carbonyl, $C_{1-12}$ haloalkoxy-carbonyl, $C_{1-12}$ alkoxy-$C_{1-12}$ alkyl, or cyano-$C_{1-12}$ alkyl preferably $R^3$ is hydrogen, $C_{1-4}$ alkyl, $C_{1-4}$ haloalkyl, $C_{3-4}$ alkenyl, $C_{1-6}$ alkyl-carbonyl, $C_{1-6}$ alkoxy-carbonyl, $C_{1-12}$ alkoxy-$C_{1-12}$ alkyl, or cyano-$C_{1-12}$ alkyl; more preferably $R^3$ is hydrogen; or $R^7$ is hydrogen, or optionally substituted $C_{1-12}$ alkyl, $C_{1-12}$ cyanoalkyl, and $C_{1-12}$ haloalkyl, optionally substituted $C_{3-8}$ cycloalkyl, $C_{3-8}$ halocycloalkyl, $C_{3-8}$ cycloalkyl-$C_{1-12}$ alkyl, and $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, amino, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino, optionally substituted aryl and aryl-$C_{1-12}$ alkyl, an optionally substituted heterocyclic group, $C_{1-12}$ alkyl substituted with a heterocyclic group, $C_{1-12}$alkylcarbonyl, $C_{1-12}$haloalkylcarbonyl or $(R^8)(R^9)N$—CO—; preferably $R^7$ is optionally substituted $C_{1-6}$ alkyl, $C_{1-6}$ cyanoalkyl, and $C_{1-6}$ haloalkyl, optionally substituted $C_{3-6}$ cycloalkyl, $C_{3-6}$ halocycloalkyl, $C_{3-6}$ cycloalkyl-$C_{1-4}$ alkyl, and $C_{3-6}$ halocycloalkyl-$C_{1-6}$ alkyl, $C_{2-6}$ alkenyl, $C_{2-6}$ haloalkenyl, $C_{1-4}$ alkoxy, $C_{1-4}$ haloalkoxy, $C_{1-4}$ alkoxy-$C_{1-4}$ alkyl, $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl, optionally substituted phenyl and phenyl-$C_{1-6}$ alkyl, methylamino, dimethylamino, ethylamino, cyclopropylamino, prop-2-yn-1-ylamino, optionally substituted heterocyclic group; more preferably $R^7$ is optionally substituted $C_{1-6}$ alkyl (in particular methyl, ethyl, propyl, iso-propyl, butyl, iso-butyl or tert.-butyl), $C_{1-6}$ cyanoalkyl (in particular cyanomethyl), $C_{1-6}$ haloalkyl (in particular ethyl, propyl, iso-propyl, butyl, iso-butyl, tert.-butyl any of which is substituted with 1 to 5 fluorine atoms and/or chlorine atoms), $C_{1-4}$ alkoxy (in particular methoxy, ethoxy, propoxy, isopropoxy, butoxy, isobutoxy, tert.-butoxy), $C_{1-4}$ haloalkoxy (in particular methoxy, ethoxy, propoxy, isopropoxy, butoxy, isobutoxy, tert.-butoxy any of which is substituted with 1 to 5 fluorine atoms and/or chlorine atoms), $C_{1-4}$ alkoxy-$C_{1-4}$ alkyl (in particular methoxy-methyl, methoxy-ethyl, ethoxy-methyl, ethoxy-ethyl), $C_{1-4}$ alkoxy-$C_{1-4}$ haloalkyl (in particular methoxy-methyl, methoxy-ethyl, ethoxy-methyl, ethoxy-ethyl in which any of the alkyl groups is optionally substituted with 1 to 5 fluorine atoms and/or chlorine atoms), $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl which are in each case optionally substituted with fluorine or chlorine atoms (in particular (methylsulfanyl)methyl, (methylsulfinyl)methyl, (methylsulfonyl)methyl any of which is optionally substituted with 1 to 5 fluorine atoms and/or chlorine atoms), methylamino, dimethylamino, ethylamino, cyclopropylamino, and prop-2-yn-1-ylamino, which are in each case optionally substituted with 1 to 5 fluorine or chlorine atoms, $C_{3-6}$ cycloalkyl optionally substituted with 1 to 5 fluorine atoms, chlorine atoms or $C_{1-4}$ haloalkyl (in particular cyclopropyl, cyclobutyl any of which is optionally substituted with 1 to 5 fluorine atoms and/or chlorine atoms and/or $C_{1-4}$ haloalkyl (e.g. $CF_3$), $C_{3-6}$ cycloalkyl-$C_{1-4}$ alkyl optionally substituted with 1 to 5 fluorine or chlorine atoms (in particular cyclopropyl-methyl, cyclopropyl-ethyl cyclobutyl-methyl, cyclobutyl-ethyl any of which is optionally substituted with 1 to 5 fluorine atoms and/or chlorine atoms), or a heterocyclic group such as $C_{3-6}$ heterocycloalkyl optionally substituted with 1 to 5 fluorine or chlorine atoms (in particular oxetan-3-yl, thietan-3-yl, 1-oxidothietan-3-yl, 1,1-dioxidothietan-3-yl any of which is optionally substituted with 1 to 5 fluorine atoms and/or chlorine atoms), phenyl or phenyl-$C_{1-4}$ alkyl which are in each case optionally substituted with 1 to 4 halogen atoms or $C_{1-4}$ haloalkyl;

$R^8$ and $R^9$ each independently are hydrogen, cyano, hydroxy, amino, $C_{1-12}$ alkyl, $C_{1-12}$ haloalkyl, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, $C_{1-12}$ alkylsulfonyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl) amino, ($C_{1-12}$ alkyl) ($C_{1-12}$ haloalkyl)amino, cyano $C_{1-12}$ alkyl, cyano-$C_{3-8}$ cycloalkyl, aryl, aryl-$C_{1-12}$ alkyl, a heterocyclic group or $C_{1-12}$ alkyl substituted with a heterocyclic group;

W is oxygen or sulfur, preferably oxygen;

E is oxygen or a $C_{1-3}$ alkanediyl-group which group can be optionally substituted by 1 or 2 $C_1$-$C_6$ alkyl groups; E is preferably a $C_{1-3}$ alkanediyl group, in particular —CH$_2$—; and $R^{6'}$ is hydrogen or $C_1$-$C_6$ alkyl; preferably $R^{6'}$ is hydrogen;

The respective compounds of formula (I) of the invention contain asymmetric carbon atoms, and therefore the compounds of the present invention encompass their respective optical isomers. The nitrogen atom on the pyrrolidine skeleton of the compounds of formula (I) of the invention may be substituted with oxygen, alkyl which may be substituted or haloalkyl which may be substituted. It may also form other salts.

DETAILED DESCRIPTION OF A PREFERRED EMBODIMENT

In a preferred embodiment [A] the invention is directed to compounds of formulae (I-A) and (I-A')

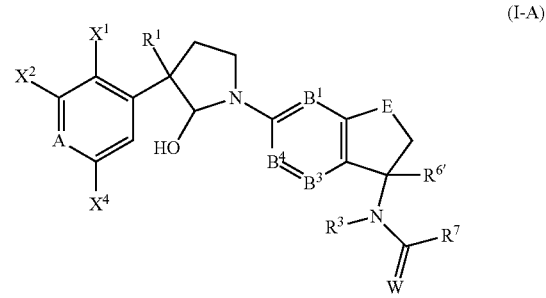

(I-A)

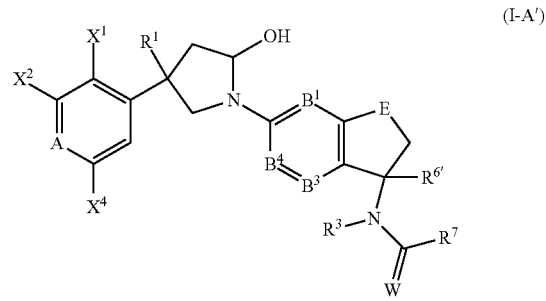

(I-A')

wherein A, W, $X^1$, $X^2$, $X^4$, $R^1$, $R^3$, $R^{6'}$, $R^7$, $B^1$, $B^3$, $B^4$ and E are as defined herein for the compounds of formula (I).

Among the compounds of embodiment [A], compounds of formulae (I-A) or (I-A') are preferred, wherein $R^1$ is $C_{1-4}$ haloalkyl; preferably $R^1$ is $CF_3$;

A is C—$X^3$ or nitrogen;

$X^1$, $X^2$, $X^3$ and $X^4$ each independently are hydrogen, fluoro, chloro, bromo or iodo or $C_{1-4}$ haloalkyl; preferably $X^1$, $X^2$, $X^3$ and $X^4$ each independently are hydrogen, fluoro, chloro, bromo or trifluoromethyl;

$B^1$ is C—H, C—F or nitrogen;

$B^3$ is C—H;

$B^4$ is C—H, or C—F or nitrogen; or $R^3$ is hydrogen, $C_{1-4}$ alkyl, $C_{1-4}$ haloalkyl, $C_{3-4}$ alkenyl, $C_{1-6}$ alkyl-carbonyl, $C_{1-6}$ alkoxy-carbonyl, $C_{1-12}$ alkoxy-$C_{1-12}$ alkyl, or cyano-$C_{1-12}$ alkyl; preferably $R^3$ is hydrogen;

$R^7$ is optionally substituted $C_{1-6}$ alkyl, $C_{1-6}$ cyanoalkyl, and $C_{1-6}$ haloalkyl, optionally substituted $C_{3-6}$ cycloalkyl, $C_{3-6}$ halocycloalkyl, $C_{3-6}$ cycloalkyl-$C_{1-4}$ alkyl, and $C_{3-6}$ halocycloalkyl-$C_{1-6}$ alkyl, $C_{2-6}$ alkenyl, $C_{2-6}$ haloalkenyl, $C_{1-4}$ alkoxy, $C_{1-4}$ haloalkoxy, $C_{1-4}$ alkoxy-$C_{1-4}$ alkyl, $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl, optionally substituted phenyl and phenyl-$C_{1-6}$ alkyl, methylamino, dimethylamino, ethylamino, cyclopropylamino, prop-2-yn-1-ylamino, optionally substituted heterocyclic group; preferably $R^7$ is optionally substituted $C_{1-6}$ alkyl (in particular methyl, ethyl, propyl, iso-propyl, butyl, iso-butyl or tert.-butyl), $C_{1-6}$ cyanoalkyl (in particular cyanomethyl), $C_{1-6}$ haloalkyl (in particular ethyl, propyl, iso-propyl, butyl, iso-butyl, tert.-butyl any of which is substituted with 1 to 5 fluorine atoms and/or chlorine atoms), $C_{1-4}$ alkoxy (in particular methoxy, ethoxy, propoxy, isopropoxy, butoxy, isobutoxy, tert.-butoxy), $C_{1-4}$ haloalkoxy (in particular methoxy, ethoxy, propoxy, isopropoxy, butoxy, isobutoxy, tert.-butoxy any of which is substituted with 1 to 5 fluorine atoms and/or chlorine atoms), $C_{1-4}$ alkoxy-$C_{1-4}$ alkyl (in particular methoxy-methyl, methoxy-ethyl, ethoxy-methyl, ethoxy-ethyl), $C_{1-4}$ alkoxy-$C_{1-4}$ haloalkyl (in particular methoxy-methyl, methoxy-ethyl, ethoxy-methyl, ethoxy-ethyl in which any of the alkyl groups is optionally substituted with 1 to 5 fluorine atoms and/or chlorine atoms), $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl which are in each case optionally substituted with fluorine or chlorine atoms (in particular (methylsulfanyl)methyl, (methylsulfinyl)methyl, (methylsulfonyl)methyl any of which is optionally substituted with 1 to 5 fluorine atoms and/or chlorine atoms), methylamino, dimethylamino, ethylamino, cyclopropylamino, and prop-2-yn-1-ylamino, which are in each case optionally substituted with 1 to 5 fluorine or chlorine atoms, $C_{3-6}$ cycloalkyl optionally substituted with 1 to 5 fluorine atoms, chlorine atoms or $C_{1-4}$ haloalkyl (in particular cyclopropyl, cyclobutyl any of which is optionally substituted with 1 to 5 fluorine atoms and/or chlorine atoms and/or $C_{1-4}$ haloalkyl (e.g. $CF_3$), $C_{3-6}$ cycloalkyl-$C_{1-4}$ alkyl optionally substituted with 1 to 5 fluorine or chlorine atoms (in particular cyclopropyl-methyl, cyclopropyl-ethyl cyclobutyl-methyl, cyclobutyl-ethyl any of which is optionally substituted with 1 to 5 fluorine atoms and/or chlorine atoms), or a heterocyclic group such as $C_{3-6}$ heterocycloalkyl optionally substituted with 1 to 5 fluorine or chlorine atoms (in particular oxetan-3-yl, thietan-3-yl, 1-oxidothietan-3-yl, 1,1-dioxidothietan-3-yl any of which is optionally substituted with 1 to 5 fluorine atoms and/or chlorine atoms), phenyl or phenyl-$C_{1-4}$ alkyl which are in each case optionally substituted with 1 to 4 halogen atoms or $C_{1-4}$ haloalkyl;

W is oxygen;

E is —CH$_2$—; and $R^{6'}$ is hydrogen.

In a further preferred embodiment the invention is directed to compounds of formulae (I-B) and (I-C)

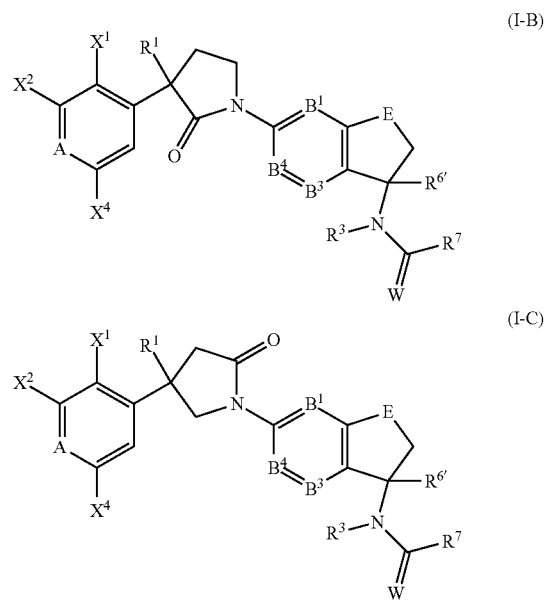

wherein A, W, $X^1$, $X^2$, $X^4$, $R^1$, $R^3$, $R^{6'}$, $R^7$, $B^1$, $B^3$, $B^4$ and E are as defined herein for the compounds of formula (I), and to the use of such compounds as intermediates, preferably in Step 2 of the preparation method (a) according to the invention, for the preparation of the compounds of formulae (I-A) and (I-A').

Thus, among the compounds of embodiment [B], compounds of formulae (I-B) and (I-C) are preferred, (which includes their use as intermediates, preferably in Step 2 of the preparation method (a) according to the invention, for the preparation of compounds of formulae (I-A) and (I-A'), wherein $R^1$ is $C_{1-4}$ haloalkyl; preferably $R^1$ is $CF_3$;

A is C—$X^3$ or nitrogen;

$X^1$, $X^2$, $X^3$ and $X^4$ each independently are hydrogen, fluoro, chloro, bromo or iodo or $C_{1-4}$ haloalkyl; preferably $X^1$, $X^2$, $X^3$ and $X^4$ each independently are hydrogen, fluoro, chloro, bromo or trifluoromethyl;

$B^1$ is C—H, C—F or nitrogen;

$B^3$ is C—H;

$B^4$ is C—H, or C—F or nitrogen; or $R^3$ is hydrogen, $C_{1-4}$ alkyl, $C_{1-4}$ haloalkyl, $C_{3-4}$ alkenyl, $C_{1-6}$ alkyl-carbonyl, $C_{1-6}$ alkoxy-carbonyl, $C_{1-12}$ alkoxy-$C_{1-12}$ alkyl, or cyano-$C_{1-12}$ alkyl; preferably $R^3$ is hydrogen;

$R^7$ is optionally substituted $C_{1-6}$ alkyl, $C_{1-6}$ cyanoalkyl, and $C_{1-6}$ haloalkyl, optionally substituted $C_{3-6}$ cycloalkyl, $C_{3-6}$ halocycloalkyl, $C_{3-6}$ cycloalkyl-$C_{1-4}$ alkyl, and $C_{3-6}$ halocycloalkyl-$C_{1-6}$ alkyl, $C_{2-6}$ alkenyl, $C_{2-6}$ haloalkenyl, $C_{1-4}$ alkoxy, $C_{1-4}$ haloalkoxy, $C_{1-4}$ alkoxy-$C_{1-4}$ alkyl, $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl, optionally substituted phenyl and phenyl-$C_{1-6}$ alkyl, methylamino, dimethylamino, ethylamino, cyclopropylamino, prop-2-yn-1-ylamino, optionally substituted heterocyclic group; preferably $R^7$ is optionally substituted $C_{1-6}$ alkyl (in particular methyl, ethyl, propyl, iso-propyl, butyl, iso-butyl or tert.-butyl), $C_{1-6}$ cyanoalkyl (in particular cyanomethyl), $C_{1-6}$ haloalkyl (in particular ethyl, propyl, iso-propyl, butyl, iso-butyl, tert.-butyl any of which is substituted with 1 to 5 fluorine atoms and/or chlorine atoms), $C_{1-4}$ alkoxy (in particular methoxy, ethoxy, propoxy, isopropoxy, butoxy, isobutoxy, tert.-butoxy), $C_{1-4}$ haloalkoxy (in particular methoxy, ethoxy, propoxy, isopropoxy, butoxy, isobutoxy, tert.-butoxy any of which is substituted with 1 to 5 fluorine atoms and/or chlorine atoms), $C_{1-4}$ alkoxy-$C_{1-4}$ alkyl (in particular methoxy-methyl, methoxy-ethyl, ethoxy-methyl, ethoxyethyl), $C_{1-4}$ alkoxy-$C_{1-4}$ haloalkyl (in particular methoxymethyl, methoxy-ethyl, ethoxy-methyl, ethoxy-ethyl in which any of the alkyl groups is optionally substituted with 1 to 5 fluorine atoms and/or chlorine atoms), $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl which are in each case optionally substituted with fluorine or chlorine atoms (in particular (methylsulfanyl)methyl, (methylsulfinyl)methyl, (methylsulfonyl)methyl any of which is optionally substituted with 1 to 5 fluorine atoms and/or chlorine atoms), methylamino, dimethylamino, ethylamino, cyclopropylamino, and prop-2-yn-1-ylamino, which are in each case optionally substituted with 1 to 5 fluorine or chlorine atoms, $C_{3-6}$ cycloalkyl optionally substituted with 1 to 5 fluorine atoms, chlorine atoms or $C_{1-4}$ haloalkyl (in particular cyclopropyl, cyclobutyl any of which is optionally substituted with 1 to 5 fluorine atoms and/or chlorine atoms and/or $C_{1-4}$ haloalkyl (e.g. $CF_3$), $C_{3-6}$ cycloalkyl-$C_{1-4}$ alkyl optionally substituted with 1 to 5 fluorine or chlorine atoms (in particular cyclopropyl-methyl, cyclopropyl-ethyl cyclobutylmethyl, cyclobutyl-ethyl any of which is optionally substituted with 1 to 5 fluorine atoms and/or chlorine atoms), or a heterocyclic group such as $C_{3-6}$ heterocycloalkyl optionally substituted with 1 to 5 fluorine or chlorine atoms (in particular oxetan-3-yl, thietan-3-yl, 1-oxidothietan-3-yl, 1,1-dioxidothietan-3-yl any of which is optionally substituted with 1 to 5 fluorine atoms and/or chlorine atoms), phenyl or phenyl-$C_{1-4}$ alkyl which are in each case optionally substituted with 1 to 4 halogen atoms or $C_{1-4}$ haloalkyl;

W is oxygen;

E is —CH$_2$—; and $R^{6'}$ is hydrogen.

In a preferred group of compounds of formula (I) n is 1 and $R^2$ is attached to the 2-position of the pyrrolidine ring.

Compounds of formulae (I-A), (I-A'), (I-B) and (I-C) exhibit a potent pesticidal effect. It is understood that terms like "compounds according to the invention" or "active compounds" refer to all compounds which can be summarized under formula (I).

Each of the above mentioned chemical groups such as $C_{1-12}$ alkyl, $C_{1-12}$ haloalkyl, $C_{1-12}$ alkoxy, $C_{1-12}$ alkoxy-$C_{1-12}$ alkyl, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkoxy-carbonyl, $C_{1-12}$ haloalkoxy-carbonyl, $C_{1-12}$ alkoxycarbonyloxy, $C_{1-12}$ haloalkoxy-carbonyloxy, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, amino, $C_{1-12}$ alkylamino, di($C_{1-12}$ alkyl) amino, $C_{1-12}$ haloalkylamino, di($C_{1-12}$ haloalkyl)amino, ($C_{1-12}$ alkyl) ($C_{1-12}$ haloalkyl)amino, aryl, aryl-$C_{1-12}$ alkyl, heterocyclic groups (such as hetoraryls or heteroalkyl), $C_{1-12}$ alkyl substituted with a heterocyclic group, $C_{1-12}$alkylcarbonyl, $C_{1-12}$haloalkylcarbonyl etc. may be substituted with a suitable substituent.

For example, $C_{1-12}$ alkyl, $C_{1-12}$ alkoxy, $C_{1-12}$ haloalkyl, $C_{1-12}$ haloalkoxy, $C_{1-12}$ alkoxy-$C_{1-12}$ alkyl and $C_{1-12}$ alkylthio-$C_{1-12}$ alkyl moieties any of which may be substituted by 1 or 2 cyano (preferably 1 cyano); or aryl and heteroaryl groups any of which may independently be substituted by 1 or 2 cyano, $C_{1-4}$ alkyl, $C_{1-4}$ haloalkyl, $C_{1-4}$ alkoxy and/or $C_{1-4}$ haloalkoxy groups and/or fluorine, chlorine, bromine (preferably independently by 1 or 2 cyano, methyl, trifluoromethyl, methoxy, difluoromethoxy or trifluoromethoxy groups, or fluorine chlorine, bromine); or $C_{3-8}$ cycloalkyl (saturated or unsaturated) may be substituted by 1 or 2 cyano, $C_{1-4}$ alkyl, $C_{1-4}$ haloalkyl and/or $C_{1-4}$ alkoxy groups and/or fluorine, chlorine; or a heterocyclic group, in particular a $C_{3-8}$ heterocycloalkyl group which preferably contains 1 or 2 oxygen and/or sulphur atoms, a SO- or SO$_2$-group and/or may optionally independently be substituted by 1 or 2 cyano, methyl, trifluoromethyl or methoxy groups, or fluorine or chlorine;

If not defined otherwise, "alkyl" represents linear or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl or n-dodecyl, preferably $C_{1-6}$ alkyl, and more preferably $C_{1-4}$ alkyl. Alkyl may be optionally substituted, preferably by 1 or 2 cyano groups.

In addition, examples of an alkyl moiety included in other groups as a part of their constitution, can be those described above for the "alkyl".

Accordingly, for example, "alkoxy" means linear or branched $C_{1-12}$ alkoxy, preferably $C_{1-6}$ alkoxy, such as methoxy, ethoxy, n-propoxy, i-propoxy, n-, iso-, sec- or tert-butoxy, pentyloxy or hexyloxy, and more preferably $C_{1-4}$ alkoxy. The alkoxy may be further substituted with a substituent, preferably with cyano.

If not defined otherwise, "haloalkyl" represents a linear or branched $C_{1-12}$ alkyl, preferably $C_{1-6}$ alkyl, more preferably $C_{1-4}$ alkyl, wherein at least one hydrogen atom of which is substituted by a halogen atom (preferably a fluorine or chlorine), such as for example $CH_2F$, $CHF_2$, $CF_3$, $CF_2Cl$, $CFCl_2$, $CF_2Br$, $CF_2CF_3$, $CFHCF_3$, $CH_2CF_3$, $CH_2CHF_2$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CFHCHF_2$, $CHFCF_3$, $CHFCF_2Cl$, $CHFCF_2Br$, $CFClCF_3$, $CCl_2CF_3$, $CF_2CF_2F_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$ and $CF_2CF_2CF_2Br$.

If not defined otherwise, "halogen" and a halogen moiety included in each group substituted with a halogen represent fluorine, chlorine, bromine or iodine, preferably fluorine, chlorine or bromine.

If not defined otherwise, "cycloalkyl" represents $C_{3-8}$ cycloalkyl, such as cyclopropyl, cyclobutyl, cyclopentyl, cyclohexyl, cycloheptyl or cyclooctyl, preferably $C_{3-7}$ cycloalkyl, and more preferably $C_{3-6}$ cycloalkyl.

If not defined otherwise, "alkenyl" represents $C_{2-12}$ alkenyl, preferably $C_{2-5}$ alkenyl, such as vinyl, allyl, 1-propenyl, 1- (or 2- or 3-)butenyl or 1-pentenyl, more preferably $C_{2-5}$ alkenyl.

If not defined otherwise, "alkynyl" represents $C_{2-12}$ alkynyl, preferably $C_{2-5}$ alkynyl, such as ethynyl, propargyl, 1-propynyl, butan-3-ynyl or pentan-4-ynyl, more preferably $C_{2-4}$ alkynyl.

If not defined otherwise, "aryl" represents a $C_{6-12}$ aromatic hydrocarbon group, for example, phenyl, naphthyl or biphenyl, preferably a $C_{6-10}$ aromatic hydrocarbon group, and more preferably phenyl.

If not defined otherwise, in the present specification "heterocycle" or "heterocyclic group" represents a 3- to 6-membered heterocyclic ring group comprising at least one of N, O and S as a hetero atom, and also represents a fused heterocyclic ring group which may be benzo-fused. Further, the heterocycle may have oxide on its N atom, if possible. According to the invention, the term "heterocycle" or "heterocyclic group" preferably stands for a $C_{3-8}$ heterocycloalkyl group which preferably contains 1 or 2 oxygen, and/or sulphur atoms, a SO- or $SO_2$-group and/or may optionally independently be substituted by 1 or 2 cyano, methyl, trifluoromethyl or methoxy groups, or fluorine or chlorine atoms.

Examples of the heterocycle include oxiranyl, thiranyl, 1-oxide thiranyl, 1,1-dioxide thiranyl, aziridinyl, oxetanyl, thietanyl, 1-oxide thietanyl, 1,1-dioxide thietanyl, azetidinyl, tetrahydrofuranyl, tetrahydrothienyl, 1-oxide tetrahydrothienyl, 1,1-dioxide tetrahydrothienyl, pyrrolidinyl, tetrahydropyranyl, piperidinyl, tetrahydrothiopyranyl, 1-oxide tetrahydrothiopyranyl, 1,1-dioxide tetrahydrothiopyranyl, furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl.

Even if not mentioned specifically, it is understood that all chemical groupings mentioned in the present application can be substituted. Suitable substituents are known to the skilled person and include among others amino, hydroxy, halogen, nitro, cyano, isocyano, mercapto, isothiocyanate, carboxy, carbamide, $SF_5$, aminosulfonyl, alkyl, cycloalkyl, alkenyl, cycloalkenyl, alkynyl, monoalkylamino, dialkylamino, N-alkylcarbonyl-amino, alkoxy, alkenyloxy, alkynyloxy, cycloalkyloxy, cycloalkenyloxy, alkoxycarbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfenyl, alkylsulfinyl, alkylsulfinyl including isomers, alkylsulfonyl, monoalkylaminosulfonyl, dialkylaminosulfonyl, alkylphosphinyl, alkylphosphonyl, alkylphosphinyl including isomers, alkylphosphonyl including isomers, N-alkyl-aminocarbonyl, N,N-dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, arylamino, benzylamino, heterocycle, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl or haloalkoxyalkyl, and preferably chloro, fluoro, bromo, iodo, amino, nitro, cyano, hydroxy, thio or carboxy.

If not defined otherwise or mentioned expressly in the present application, the term "in the agricultural field" refers to the protection of plants or plant parts. Livestock farming is not included.

If not defined otherwise or mentioned expressly in the present application, the term "controlling" or "combating" means that the active compounds according to the invention are effective in reducing the incidence of the respective agricultural pests on plants, or plant parts (such as seeds). More specifically, "controlling" or "combating" as used herein, means that the active compound is effective in killing the respective pest, inhibiting its growth, or inhibiting its proliferation.

The expression "active compound" or "compounds according to the invention" are used synonymously herein.

The invention is further directed to a preparation method (c) for the preparation of a compound of formula (I-A), (I-A'), (I-B) and (I-C)

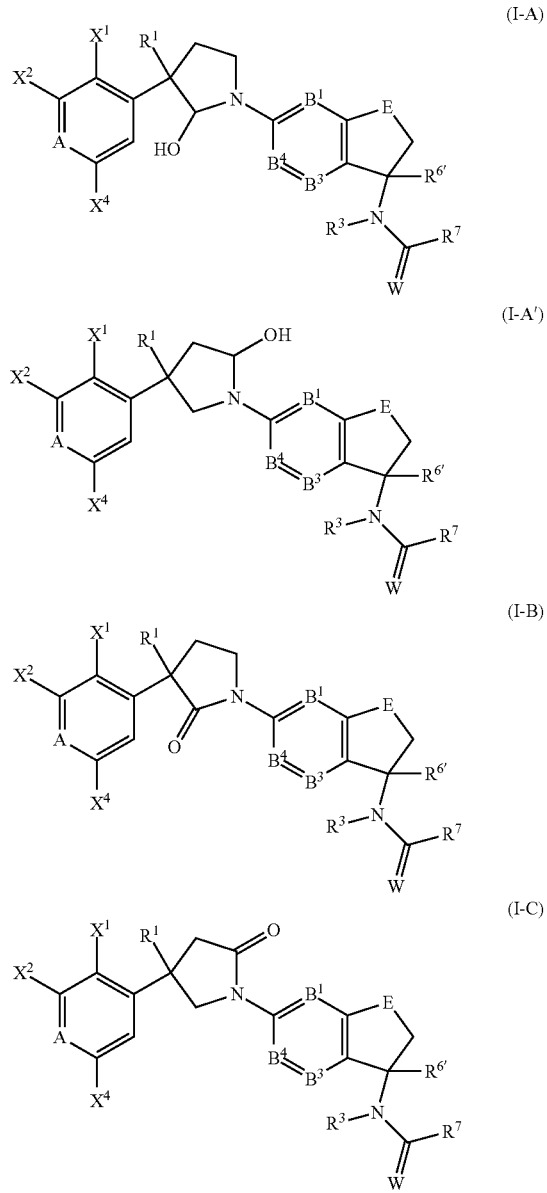

comprising the oxidation of a compound of formula (II)

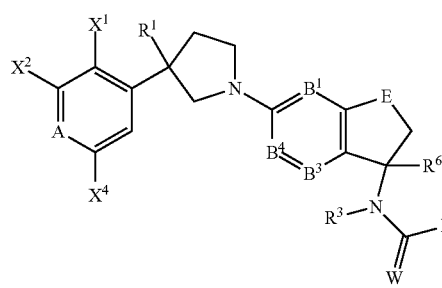

wherein in the compound of formulae (I-A), (I-A'), (I-B), (I-C) and (II) $X^1$, $X^2$, A, $X^4$, $R^1$, $R^3$, $R^{6'}$, $R^7$, $B^1$, $B^3$, $B^4$, E and W are as defined herein, with an oxidation agent, under appropriate reaction conditions, optionally in the presence of a catalyst.

Suitable oxidation agents comprise $H_2O_2$, $MnO_2$, $KMnO_4$, $RuO_4$, peracids (e.g. m-chloroperbenzoic acid (MCPBA)), quinones (e.g. 2,3-dichloro-5,6-dicyano-1,4-benzoquinone (DDQ), tetrachloro-1,2-benzoquinone (o-Chloranil), tetrachloro-1,4-benzoquinone (Chloranil)), cerium(IV)salts (e.g. ceric(IV)ammonium nitrate (CAN)) or silver(II)salts (such as inorganic or organic silver(II)salts (e.g. silver(II)fluoride, bis($\alpha,\alpha'$-bipyridine)silver(II)nitrate, bis($\alpha,\alpha'$-bipyridine)silver(II)peroxydisulfate, silver(II)picolinate, and tetrakis(pyridine)silver(II)), hypervalent iodine compounds (e.g. [bis(trifluoroacetoxy)iodo]benzene, [bis(acetoxy)iodo]benzene, iodosobenzene, 2-iodoxybenzoic acid, pentafluoroiodosobenzene) and air (oxygen).

Suitable catalysts are transition metal catalysts (e.g. N',N'-bis(salicylidene)ethylenediamine iron (II)), an acid catalyst (e.g. acetic acid, trifluoroacetic acid, silica gel) or a phase transfer catalyst (e.g. benzyltriethylammonium chloride, tetrabutylammonium bromide, crown ether).

In an embodiment of before mentioned preparation method (c), the compound of formula (I-B) or (I-C) can be converted into the respective compound of formula (I-A) or (I-A'). For this conversion, the compound of formula (I-B) or (I-C) is isolated using routine methods and then reacted with a reducing agent, such as e.g. sodium tetrahydroborate, lithium tetrahydroborate, lithium aluminum hydride, diisobutylaluminum hydride, or super hydride), if necessary, in the presence of an appropriate diluent. This embodiment which includes preparation method (c) as Step 1 and a reduction as Step 2 will be further summarized under "preparation method (a)".

An oxidation reaction of pyrrolidine ring by using $KMnO_4$ and benzyltriethylammonium chloride as a phase transfer catalyst in dichloromethane is described by Markgraf and Stickney in Journal of Heterocyclic Chemistry, 2000 (37), 109-110.

Kaname et al. describes in Tetrahedron Letters, 2008(49), 2786-2788, an oxidation reaction to oxidize N-acyl pyrrolidine with $RuO_2$ and using $NaIO_4$ as co-oxidant and ethyl acetate system.

Preparation Method (a)

A method in which, in a Step 1, the compounds represented by formula (II):

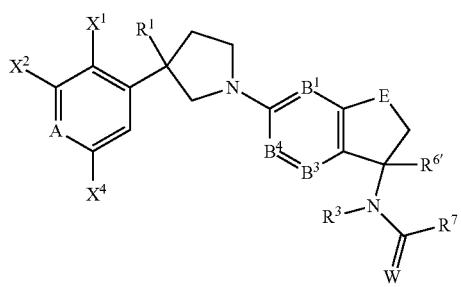

wherein $X^1, X^2, A, X^4, R^1, R^3, R^{6'}, R^7, B^1, B^3, B^4, E$ and $W$ are as defined above, are reacted with an oxidizing agent, such as e.g. manganese dioxide, potassium permanganate, ruthenium tetraoxide, if necessary, in the presence of an appropriate diluent to give the compounds represented by formula (I-B):

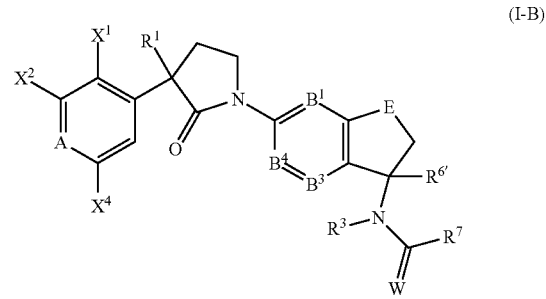

and/or the compounds represented by formula (I-C):

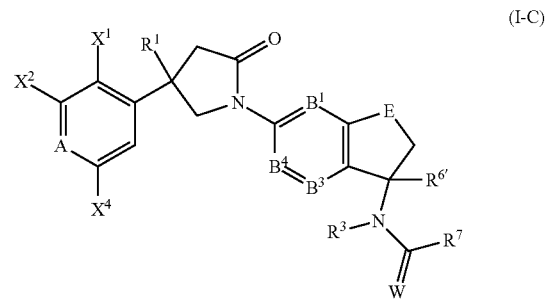

wherein $X^1, X^2, A, X^4, R^1, R^3, R^{6'}, R^7, B^1, B^3, B^4, E$ and $W$ are as defined herein for these compounds and subsequently, in a Step 2, they are reacted with a reducing agent, such as e.g. sodium tetrahydroborate, lithium tetrahydroborate, lithium aluminum hydride, diisobutylaluminum hydride, or super hydride, if necessary, in the presence of an appropriate diluent, to give the compounds represented by formula (I-A):

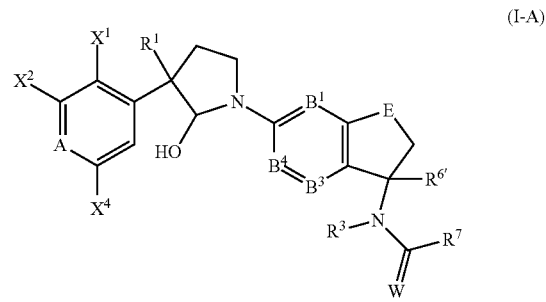

and/or the compounds represented by formula (I-A'):

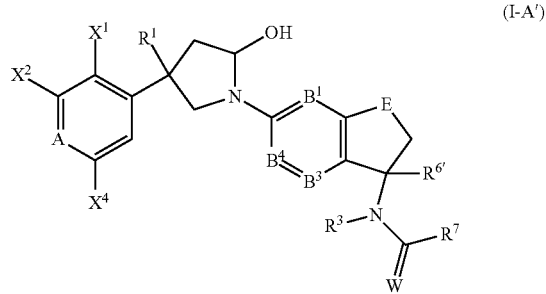

wherein $X^1, X^2, A, X^4, R^1, R^3, R^{6'}, R^7, B^1, B^3, B^4, E$ and $W$ are as defined above.

The reaction of Step 1 in the preparation method (a) can be carried out in the presence of a catalyst, such as e.g. a transition metal catalyst (e.g. N',N'-bis(salicylidene)ethylenediamine iron (II)), an acid catalyst (e.g. acetic acid, trifluoroacetic acid, silica gel) or a phase transfer catalyst (e.g. benzyltriethylammonium chloride, tetrabutylammonium bromide, crown ether) (cf. Journal of Heterocyclic Chemistry, 2000(37), 109-110 and Tetrahedron Letters, 2008(49), 2786-2788).

Diluents which can be used in the reaction of Step 1 in the preparation method (a) are for example aliphatic hydrocarbons (e.g. hexane, cyclohexane, heptane), aliphatic halogenated hydrocarbons (e.g. dichloromethane, chloroform, carbon tetrachloride, dichloroethane), aromatic hydrocarbons (e.g. benzene, toluene, xylene, chlorobenzene), ethers [e.g. diethyl ether, dibutyl ether, dimethoxyethane (DME), tetrahydrofuran, dioxane], esters (e.g. ethyl acetate, ethyl propionate), acid amides [e.g. dimethylformamide (DMF), dimethylacetamide (DMA), N-methylpyrrolidone], nitriles (e.g. acetonitrile, propionitrile), dimethylsulfoxide (DMSO), water or a mixture of the diluents.

Step 1 in the preparation method (a) can be carried out over a substantially wide range of temperatures. It may be generally carried out at the temperature ranging from about −78° C. to about 200° C., preferably from about −10° C. to about 150° C. Furthermore, the reaction is preferably carried out under normal pressure. However, it may be carried out under reduced or elevated pressure. The reaction time is 0.1 to 72 hours, preferably 0.1 to 24 hours.

In carrying out Step 1 of the preparation method (a), for example, a compound of formula (I-B) and/or formula (I-C) can be obtained by reacting relative to 1 mole of a compound of formula (II) with 1 to 5 molar amounts of an oxidizing agent, such as potassium permanganate, in the presence of 1 to 5 molar amounts of a phase transfer catalyst, such as benzyltriethylammonium chloride, in a diluent, such as dichloromethane.

Diluents which can be used in the reaction of Step 2 in the preparation method (a) are for example aliphatic hydrocarbons (e.g. hexane, cyclohexane, heptane), aliphatic halogenated hydrocarbons (e.g. dichloromethane, chloroform, carbon tetrachloride, dichloroethane), aromatic hydrocarbons (e.g. benzene, toluene, xylene, chlorobenzene), ethers (e.g. diethyl ether, dibutyl ether, dimethoxyethane (DME), tetrahydrofuran, dioxane), alcohols (e.g. methanol, ethanol, isopropanol, tert-butyl alcohol), water or a mixture of the diluents.

The reaction of Step 2 of the preparation method (a) can be carried out over a substantially wide range of temperatures. It may be generally carried out at the temperature ranging from about −100° C. to about 200° C., preferably from −78° C. to 100° C. Furthermore, the reaction is preferably carried out under normal pressure. However, it may be carried out under reduced or elevated pressure. The reaction time is 0.1 to 72 hours and preferably 0.1 to 24 hours.

In carrying out Step 2 of the preparation method (a), for example, a compound of formula (I-A) or formula (I-A') can be obtained by reacting relative to 1 mole of the compound of formula (I-B) or formula (I-C) with 1 to 10 molar amounts of a reducing agent, such as diisobutylaluminum hydride, in a diluent, such as dichloromethane.

Similar reactions are described in Organic Letters, 2010, 1252-1254; Tetrahedron, 1999, 5623-5634, and Journal of the Organic Chemistry, 2008, 3946-3949.

The invention is further directed to a method wherein compounds of formula (II) are oxidized in one step to obtain compounds of formula (I-A) and/or formula (I-A'). This method will be further summarized under "preparation method (b)".

The reaction of the preparation method (b) can be carried out in the presence of an appropriate diluent, and examples of the diluent which can be used include aliphatic hydrocarbons (hexane, cyclohexane, heptane), halogenated aliphatic hydrocarbons (dichloromethane, chloroform, carbon tetrachloride, dichloroethane), aromatic hydrocarbons (benzene, toluene, xylene, chlorobenzene), ethers (diethyl ether, dibutyl ether, dimethoxyethane (DME), tetrahydrofuran, dioxane), esters (ethyl acetate, ethyl propionate, etc.), acid amides (dimethylformamide (DMF), dimethylacetamide (DMA), N-methylpyrrolidone), nitriles (acetonitrile, propionitrile), dimethyl sulfoxide (DMSO), tert-butyl alcohol, carboxylic acids (acetic acid, propionic acid, trifluoroacetic acid), water or a mixture of the diluents.

Similar to Step 1 of preparation method (a), the oxidation reaction in preparation method (b) can be carried out by using an oxidizing agent such as manganese dioxide, cerium ammonium nitrate (IV) (CAN), 2,3-dichloro-5,6-dicyano-1,4-benzoquinone (DDQ), tetrachloro-1,2-benzoquinone (o-Chloranil), tetrachloro-1,4-benzoquinone (Chloranil), iodosobenzene, pentafluoroiodosobenzene, hydrogen peroxide, air (oxygen).

Similar to Step 1 of the preparation method (a), the reaction of the preparation method (b) can be also carried out, if necessary, by using a catalyst, such as a transition metal catalyst (e.g. N',N'-bis(salicylidene)ethylenediamine iron (II)), or an acid catalyst (e.g. acetic acid, trifluoroacetic acid, silica gel).

Similar reactions are described in Heterocycles, 2003, 551-555; Tetrahedron Letters, 1983, 2213-2216; Journal of the Organic Chemistry, 1991, 1981-1983 and Chemical & Pharmaceutical Bulletin, 1990, 532-533.

The reaction of the preparation method (b) can be carried out over a substantially wide range of temperatures. It may be generally carried out at the temperature ranging from about −78° C. to about 200° C., preferably from about −10° C. to about 150° C. Furthermore, the reaction is preferably carried out under normal pressure. However, it may be carried out under reduced or elevated pressure. The reaction time is up to 72 hours, preferable 0.1 to 72 hours, and more preferably 0.1 to 24 hours.

For carrying out the preparation method (b), for example, a compound of formula (I-A) which is within the compounds of the formula (I) of the invention can be obtained by reacting relative to 1 mole of the compound of formula (II) with 1 to 5 molar amounts of an oxidizing agent, such as iodosobenzene, in a diluent, such as dichloromethane, in the presence of 0.01 to 1 molar amounts of N',N'-bis(salicylidene)ethylenediamine iron (II).

Preferred compounds of formula (II) to be used for the preparation method (a) or (b) according to the invention are compounds of formulae (II-a) to (II-d), wherein $X^1$, $X^2$, $X^3$, $X^4$, and $Y^2$, $R^3$, $R^4$, $R^5$, $R^7$ are as defined herein for the compounds of formula (I) or the compounds of formulae (I-A), (I-A'), (I-B), (I-C).

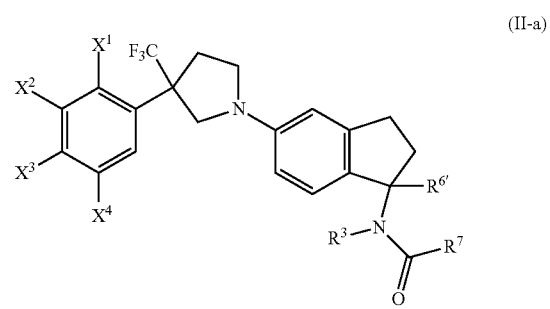
(II-a)

(II-b)

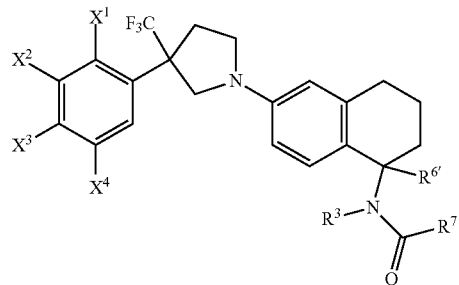

(II-c)

(II-d)

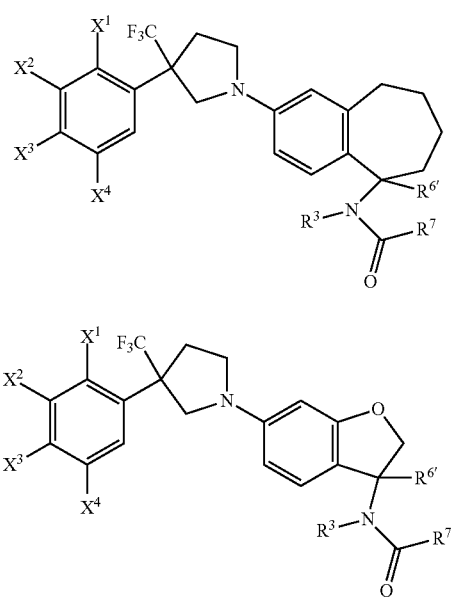

Precursors of formulae (II-a) and (II-b), which are used as starting materials in the preparation methods according to the invention are known from WO 2010/043315, precursors of formulae (II-c) and (II-d) can be prepared according to the methods described in in WO 2010/043315.

Example of Step 1 of the Preparation Method (a)

Oxidation of N-{5-[3-(3,4,5-trichlorophenyl)-3-(trifluoromethyl)pyrrolidin-1-yl]-2,3-dihydro-1H-inden-1-yl}cyclopropanecarboxamide with potassium permanganate KMnO$_4$

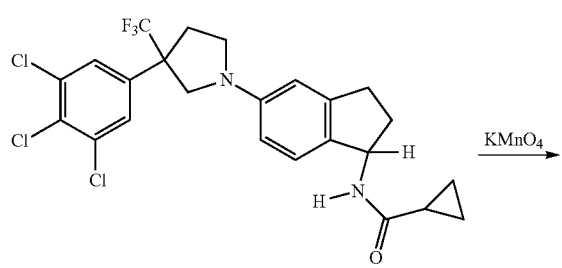

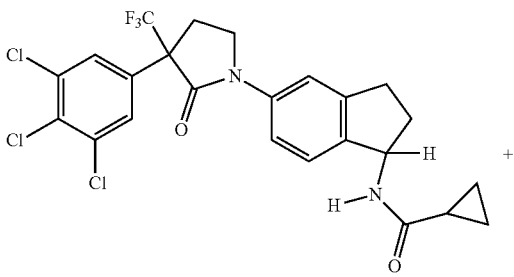

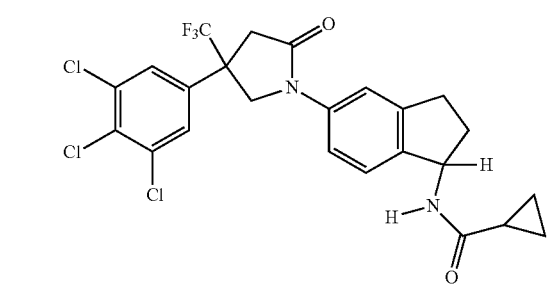

Example of Step 2 of the Preparation Method (a)

Reduction of N-(6-{3-[3,5-bis(trifluoromethyl)phenyl]-2-oxo-3-(trifluoromethyl)pyrrolidin-1-yl}-1,2,3,4-tetrahydronaphthalen-1-yl)acetamide with diisobutylaluminum hydride

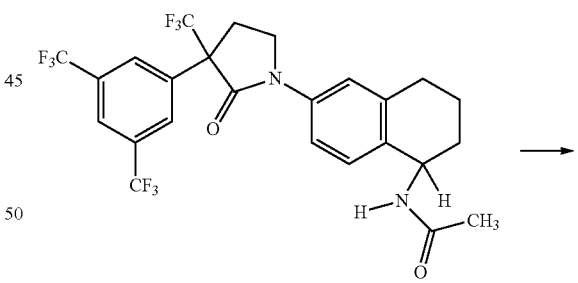

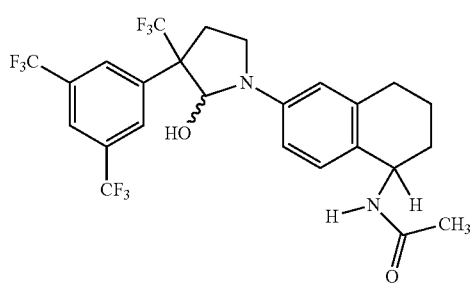

Example of the Preparation Method (b)

Reacting N-{5-[3-(3,5-dichloro-2,4-difluorophenyl)-3-(trifluoromethyl)pyrrolidin-1-yl]-2,3-dihydro-1H-inden-1-yl}propanamide, with a reducing agent, namely N',N'-bis(salicylidene)ethylenediamine iron (II) and iodosobenzene

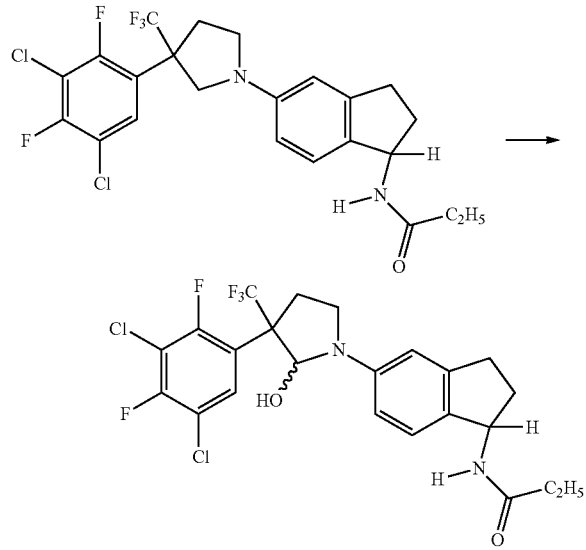

Compounds of the formula (II), which are used as starting materials in the preparation methods (a) and (b) according to the invention, are known and can be prepared according to the methods described in WO 2008/128711, WO 2010/020522, WO 2010/043315, WO 2011/080211, JP 2008-110971A.

Preferred intermediates of formulae (II-a) and (II-b) according to the present invention for the manufacturing of the compounds of formula (I) are described in the experimental part of the specification.

The compounds of formula (I) of the invention exhibit a potent pesticidal effect, and therefore can be used as pesticides. Furthermore, the compounds of the invention exhibit a potent controlling effect against noxious insects without causing any damages on crop plants that are cultivated. Therefore, the compounds of the invention can be used for controlling a wide variety of pests including, for example, harmful sucking insects, chewing insects and other plant parasitic pests, stored grain insects, hygienic pests, etc., and can be applied to control and eradicate these pests. Examples of animal pests are as follows:

As an insect, Coleoptera, for example *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus* and *Aulacophora femoralis*; Lepidoptera, for example, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens* and *Phyllocnistis citrella*; Hemiptera, for example, *Nephotettix cincticeps, Nilaparvata lugens, Pseudococcus comstocki, Unapsis yanonensis, Myzus persicas, Aphis pomi, Aphis gossypii, Rhopalosiphum pseudobrassicas, Stephanitis nashi, Nezara* spp., *Trialeurodes vaporariorm* and *Psylla* spp.; Thysanoptera, for example, *Thrips palmi* and *Franklinella occidental*; Orthoptera, for example, *Blatella germanica, Periplaneta americana, Gryllotalpa Africana* and *Locusta migratoria* migratoriodes; Isoptera, for example, *Reticulitermes speratus* and *Coptotermes formosanus*; Diptera, for example, *Musca domestica, Aedes aegypti, Hylemia platura, Culex pipiens, Anopheles sinensis, Culex tritaeniorhynchus* and *Liriomyza torifolii*. As acarina, for example, *Tetranychus cinnabarinus, Tetranychus urticae, Panonychus citri, Aculops pelekassi* and *Tarsonemus* spp. As nematodes, for example, *Meloidogyne incognita, Bursaphelenchus lignicolus Mamiya et Kiyohara, Aphelenchoides besseyi, Heterodera glycines* and *Pratylenchus* spp.

Further, the compounds of the present invention have good tolerance in plants and low toxicity to warm-blooded animals, as well as being well received by an environment, and accordingly, the compounds of the present invention are appropriate for the protection of plants and plant parts. With application of the compounds of the present invention, both crop yield and quality of harvested products may be improved. In addition, the compounds of the present invention are suitable for protection of preserved products and materials and for a hygiene field, in terms of controlling harmful animals, in particular insects, spider-like animals, helminth, nematodes and mollusks that are encountered in agriculture, horticulture, veterinary medicine, forest, garden and entertainment facilities. The compounds of the present invention can be preferably used as agents for protecting plants. The compounds of the present invention have an activity for normal sensitive species or resistant species, and for all over or several growth stages thereof. In particular, the harmful organisms mentioned above include the followings. From Anoplura (Phthiraptera), for example, *Damalinia* spp., *Haematopinus, Linognathus* spp., *Pediculus* spp. and *Trichodectes* spp. From Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranyctus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp. and *Vasates lycopersici*. From Bivalva, for example, *Dreissena* spp. From Chilopoda, for example, *Geophilus* spp. and *Scutigera* spp. From Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp.,

*Sphenophorus* spp., *Sternechus* spp., *Symphyletes* spp., *Tenebrio molitor*, *Tribolium* spp., *Trogoderma* spp., *Tychius* spp., *Xylotrechus* spp. and *Zabrus* spp. From Collembola, for example, *Onychiurus armatus*). From Dermaptera, for example, *Forficula auricularia*). From Diplopoda, for example, *Blaniulus guttulatus*). From Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa* and *Wohlfahrtia* spp. From Gastropoda, for example, *Anon* spp., *Biomphalaria* spp., *Bulinus* spp., *Deroceras* spp., *Galba* spp., *Lymnaea* spp., *Oncomelania* spp. and *Succinea* spp. From helminthes, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medeinensis*, *Echinococcus granulosus*, *Echinococcus multiocularis*, *Enterobius vermicularis*, *Faciola* spp., *Haemonchus* spp., *Heterakis* spp., *Hymenolepis nana*, *Hyostrongulus* spp., *Loa boa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*) and *Wuchereria bancrofti*. Further, Protozoa, such as *Eimeria*, can be controlled by the compound of the present invention. From Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus*, spp., *Euschistus* spp., *Eurygaster* spp., *Heliopeltis* spp., *Horchias nobiellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodonius* spp., *Sahlbergella singularis*, *Scotinophora* spp., *Stephanitis nashi*, *Tibraca* spp. and *Triatoma* spp. From Homoptera, for example, *Acyrthosipon* spp., *Aeneolamia* spp., *gonoscena* spp., *Aleurodes* spp., *Aleurolobus barodensis*), *Aleurothrixus* spp., *Amrasca* spp., *Anuraphis cardui*, *Aonidiella* spp., *Aphanostigma pin*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Chryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratorioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesda gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp. and *Viteus vitifolii*. From Hymenoptera, for example, *Diprion* spp., *Hoplocampa* spp., *Lasius* spp., *Monomorium pharaonis*) and *Vespa* spp. From Isopoda, for example, *Armadillidium vulgare*, *Oniscus asellus* and *Porcellio scaber*. From Isoptera, for example, *Reticulitermes* spp. and *Odontotermes* spp. From Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana* and *Trichoplusia* spp. From Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta Americana* and *Schistocerca gregaria*. From Siphonaptera, for example, *Ceratophyllus* spp. and *Xenopsylla cheopis*. From Symphyla, for example, *Scutigerella immaculate*. From Thynsanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni* and *Thrips* spp. From Thysanura, for example, *Lepisma saccharina*. As plant parasitic nematodes, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Thlenchulus semipenetrans* and *Xiphinema* spp. are included.

Additionally to above mentioned, the active compounds according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in protection of stored products and of materials, and in the hygiene sector. They can be preferably employed as plant protection agents. They are active against normally sensitive and resistant species and against all or some stages of development. The abovementioned pests include:

pests from the phylum Arthropoda, especially from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici*;

from the class Chilopoda, for example, *Geophilus* spp., *Scutigera* spp.;

from the order or the class Collembola, for example, *Onychiurus armatus*;

from the class Diplopoda, for example, *Blaniulus guttulatus*;

from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order Coleoptera, for example, Acalymma *vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;

from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order Homoptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosi-*

*phum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis, Sirex* spp., *Solenopsis invicta, Tapinoma* spp., *Urocerus* spp., *Vespa* spp., *Xeris* spp.;

from the order Isopoda, for example, *Armadillidium vulgare, Oniscus asellus, Porcellio scaber;* from the order Isoptera, for example, *Coptotermes* spp., *Cornitermes cumulans, Cryptotermes* spp., *Incisitermes* spp., *Microtermes obesi, Odontotermes* spp., *Reticulitermes* spp.;

from the order Lepidoptera, for example, *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order Orthoptera or Saltatoria, for example, *Acheta domesticus, Dichroplus* spp., *Gryllotalpa* spp., *Hieroglyphus* spp., *Locusta* spp., *Melanoplus* spp., *Schistocerca gregaria;* from the order Phthiraptera, for example, *Damalinia* spp., *Haematopinus* spp., *Linognathus* spp., *Pediculus* spp., *Ptirus pubis, Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans, Tunga penetrans, Xenopsylla cheopsis;* from the order Thysanoptera, for example, *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order Zygentoma (=Thysanura), for example, *Ctenolepisma* spp., *Lepisma saccharina, Lepismodes inquilinus, Thermobia domestica;* from the class Symphyla, for example, *Scutigerella* spp.;

pests from the phylum Mollusca, especially from the class Bivalvia, for example, *Dreissena* spp., and from the class Gastropoda, for example, Anion spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests from the phylums Plathelminthes and Nematoda, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* phytoparasitic pests from the phylum Nematoda, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

It is furthermore possible to control organisms from the subphylum Protozoa, especially from the order Coccidia, such as *Eimeria* spp.

Any kind of plant and plant part can be treated according to the present invention. In the present invention, a plant should be understood as all plants and plant populations including desirable and undesirable wild plants or crop plants (including naturally-occurring crop plants) and the like. As for the crop plants, they can be plants which are obtainable by conventional methods of breeding modified varieties and optimization methods, or biotechnological methods and genetic engineering methods, or by combination of these methods, and they include transgenic plants. In addition, plant varieties which are either protected or not protected by a plant breeder are also included. Plant parts should be understood as all parts and organs of a plant that are present above or under ground. Examples thereof include shoots, leaves, flowers and roots, etc. Specific examples thereof include a leaf, a needle, a stem, a trunk, a flower, a fruit, a fruit body, a seed, a root, a tuber and an underground tuber, etc. The plant parts also include a harvested material and a material which propagates sexually or asexually, for example, a cutting, a tuber, an underground tuber, a side branch and a seed.

Treatment of plants and plant parts with the active compounds according to the present invention can be carried out directly or by using conventional methods such as impregnation, spray, evaporation, particularization, dispersion, coating and injection, or for a propagating material, especially for a seed, by coating it with one or more of the compounds, so that the compounds are applied to their surroundings, habitat environment, or preservation place.

The compounds of the present invention have a penetrating activity and this means that the compounds can penetrate a plant body and can migrate from the underground part to the above-ground part of a plant.

As it has been described above, according to the present invention, all plants and parts thereof can be treated. According to a preferred embodiment for carrying out the invention, wild plant species and plant mutants, or those obtained by traditional plant breeding methods such as hybridization or protoplast fusion, and parts thereof are treated. According to a more preferred embodiment for carrying out the invention, transgenic plants and plant varieties (genetically modified organisms) obtained by conventional methods in appropriate combination with genetic engineering methods, and parts thereof are treated. The terms "parts", "parts of a plant" and "plant parts" are as defined above. Still more preferably, for each specific case, plants of plant varieties that are commercially available or currently in use are treated according to the present invention. Plant varieties are understood as plants having new characteristics ("traits") obtained by conventional breed improvements, introduction of mutation or recombinant DNA techniques. They can be plant varieties, biotypes or genotypes. Depending on plant species or plant varieties, their habitat and growth condition (soil, weather, growth period, nutrition, etc.), the treatment according to the present invention may have a supra-additive ("synergy") effect. Thus, for example, exceeding an expected effect, it is possible to obtain several effects including reduction of application rate and/or broadening of an activity spectrum, and/or increased activity of the material and composition that can be used according to the present invention, improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products. The preferable transgenic plants or plant varieties (obtainable by genetic engineering methods) treated according to the present invention include all kinds of plant having genetic materials that can provide the plants with very advantageous and useful traits based on genetic modifications. Examples of such traits include improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products. Further examples in which such traits are particularly more emphasized include improved protection of plants against harmful animals and harmful microorganisms such as insect, tick, plant pathogenic fungus, bacteria and/or virus, and improved tolerance of plants against compounds having certain type of herbicidal activities. Examples of the transgenic plant include grain crops (barley, rice), corn, soybean, potato, sugar beet, tomato, bean and other modified plant species, useful plants such as cotton, tobacco, rape seed, and fruit plants (fruits like an apple, a pear, a citrus fruit and other fruit-bearing plants like a grape). In particular, corn, soybean, potato, cotton, tobacco and rape seed are important. As for the traits considered to be important, improved plant defense based on toxins produced by plants, in particular based on the toxins produced by plants with an action of genetic materials derived from *Bacillus thuringiensis* (for example, genes including CryIA (a), CryIA(b), CryIA(c), CryIIA, CryIIIA, CryIIIB2, Cry9c, Cry2Ab, Cry3Bb and CryIF, and combination thereof), against insects, spider-like animals, nematodes, slugs, and snails (herein below, referred to as "Bt plant") can be mentioned. Other traits considered to be important include improved plant defense against fungus, bacteria and virus, based on systemic acquired resistance (SAR), systemin, phytoallexin, elicitor, resistance gene and the corresponding protein and toxin expressed from the gene. Further, particularly important traits are improved tolerance of plants to a certain kind of an active compound having a herbicidal activity, such as imidazolinone, sulfonyl urea, glyphosate or phosphinotricine (e.g., "PTA" gene). Genes which can endow desired traits to a subject can also be present in combination each other in a transgenic plant. Examples of the "Bt plant" include modified varieties of corn, modified varieties of cotton and modified varieties of potato that are commercially available under the trade names of YIELD GARD® (for example, corn, cotton, soybean), KnockOut® (for example, corn), StarLink® (for example, corn), Bollgard® (cotton), Nucotn® (cotton) and New Leaf® (potato), respectively. Examples of the plant having resistance to herbicides include modified varieties of corn, modified varieties of cotton and modified varieties of potato that are commercially available under the trade names of Roundup Ready® (resistance to glyphosate, for example, corn, cotton, soybean), Liberty Link® (resistance to phosphinotricine, for example rape seed), IMI® (resistance to imidazolinones) and STS® (resistance to sulfonylurea, for example, corn), respectively. Examples of the plant having resistance to herbicides (i.e., the plant obtained by conventional breeding methods to have resistance to herbicides) also include modified varieties, for example those that are commercially available under the trade name of Clearfield® (for example, corn). Of course, these descriptions are also applied to plant varieties which have already had genetic traits or will have genetic traits to be developed in future. Such plant varieties will be developed and/or on the market in future.

Additionally to above mentioned, according to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782, 096, 11/657,964, 12/192,904, 11/396,808, 12/166,253, 12/166,239, 12/166,124, 12/166,209, 11/762,886, 12/364, 335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes. Plants expressing EPSPS genes that confer glyphosate tolerance are described. Plants comprising other genes that confer glyphosate tolerance, such as decarboxylase genes, are described.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). HPPD is an enzyme that catalyzes the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712). The production of sulfonylurea-tolerant plants and imidazolinone-tolerant plants is described. Other imidazolinone-tolerant plants are also described. Further sulfonylurea- and imidazolinone-tolerant plants are also described.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uldhome/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants.

2) plants which contain a stress tolerance enhancing transgene capable of reducing the expression and/or the activity of the PARG encoding genes of the plants or plants cells.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha-1,4-glucans, plants producing alpha-1,6 branched alpha-1,4-glucans, plants producing alternan.

3) transgenic plants which produce hyaluronan.

4) transgenic plants or hybrid plants, such as onions with characteristics such as 'high soluble solids content', 'low pungency' (LP) and/or 'long storage' (LS).

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes
b) Plants, such as cotton plants, containing an altered form of rsw2 or rsw3 homologous nucleic acids Plants, such as cotton plants, with increased expression of sucrose phosphate synthase
c) Plants, such as cotton plants, with increased expression of sucrose Plants, such as cotton plants, wherein the timing of the plasmodesmatal gating at the basis of the fiber cell is altered, e.g. through downregulation of fiber-selective β-1, 3-glucanase
d) Plants, such as cotton plants, having fibers with altered reactivity, e.g. through the expression of N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
a) Plants, such as oilseed rape plants, producing oil having a high oleic acid content
b) Plants such as oilseed rape plants, producing oil having a low linolenic acid content
c) Plant such as oilseed rape plants, producing oil having a low level of saturated fatty acids Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with *APHIS* or granted by *APHIS* were those containing the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://cera-gmc.org/index.php?evidcode=&hstIDXCode=& gType=&AbbrCode=&atCode=&stCode=&coIDCode=& action=gm_crop_database&mode=Submit).

With the compounds of the present invention at appropriate concentration, the plants mentioned above can be advantageously treated, in particular.

In particular, the following conventional or GMO-plants as well as their seeds or their propagation material can be treated with the compound according to the invention: cotton, corn, maize, soybean, wheat, barley, oil seed rape, tobacco, banana, vine, rice, cereals, fruits and vegetables (such as aubergine, pome fruit, stone fruit, soft fruit, cucumber, pear, bell pepper, melons, cabbage, potato, apple) and turf.

Further, in a veterinary medicine field, the novel compounds of the present invention can be effectively used against various harmful animal parasites (endo- and ectoparasites), for example, insects and helminths. Examples of such harmful animal parasites include the harmful organisms as follows. As insects, there are for example, *Gasterophilus* spp., *Stomoxys* spp., *Trichodectes* spp., *Rhodnius* spp., *Ctenocephalides canis*, *Cimx lectularius*, *Ctenocephalides felis*, *Lucilia cuprina* and the like. As Acarina, there are for example, *Ornithodoros* spp., *Ixodes* spp., *Boophilus* spp. and the like.

In a field of veterinary, i.e., in a veterinary medicine field, the active compounds of the present invention show an activity against parasites, in particular endoparasites and ectoparasites. The term "endoparasites" especially include helminths such as tapeworms, nematodes, and trematodes and protozoas such as coccidian. Ectoparasites include, typically and also preferably, arthropods, in particular, insects such as fly (biting fly and sucking fly), larva of parasitic fly, louse, pubic louse, bird louse, and flea, and mites of Acarina such as hard tick or soft tick, sarcoptic mite, chigger mite and bird mite.

These parasites include the followings:

From Anoplurida, for example, *Haematopinus* spp., *Linognathus* spp., *Pediculus* spp., *Phtirus* spp. and *Solenopotes* spp., and specific examples thereof include *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis* and *Solenopotes capillatus.*

From Mallophagida, Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. *and Felicola* spp., and specific examples include *Bovicola bovis, Bovicola ovis, Bovicola limbata, Damalina bovis, Trichodectes canis, Felicola subrostratus, Bovicola caprae, Lepikentron ovis*) and *Werneckiella equi*.

From Diptera, Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitora* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.) and *Rhinoestrus* spp., *Tipula* spp. and specific examples include *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melphagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis), Gasterophilus pecorum*) and *Braulra coeca*.

From Siphonapterida, for example, *Pulex* spp., *Ctenocephalides* spp., *Tunga* spp., *Xenopsylla* spp. and *Ceratophyllus* spp., and specific examples include *Ctenocephalides canis, Ctenocephalides felis, Pulex irritans, Tunga penetrans* and *Xenopsylla cheopsis*.

From Heteropterida, for example, *Cimex* spp., *Triatoma* spp., *Rhodnius* spp. and *Panstrongylus* spp.

From Blattarida, for example, *Blatta orientalis, Periplaneta americana, Blattela germanica*) and *Supella* spp., for example, *Supella longipalpa*.

From Acari (Acarina), and Metastigmata and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp.)(original genus of heteroxenous mites), *Ornithonyssus* spp., *Pneumonyssus* spp., *Raillietia* spp., *Pneumonyssus* spp., *Sternostoma* spp., *Varroa* spp. and *Acarapis* spp., and specific examples include *Argas persicus, Argas reflexus, Ornithodorus moubata, Otobius megnini, Rhipicephalus(Boophilus)microplus, Rhipicephalus(Boophilus)decoloratus, Rhipicephalus(Boophilus) annulatus, Rhipicephalus*(Boo-philus)calceratus, *Hyalomma annatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum* and *Varroa jacobsoni*).

From Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp.) and *Laminosioptes* spp., and examples thereof include *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae, Sarcoptes equi, Sarcoptes suis, Psoroptes ovis, Psoroptes cuniculi, Psoroptes equi, Chorioptes bovis, Psoergates ovis*, Pneumonyssoidic mange, *Pneumonyssoides caninum* and *Acarapis woodi*.

The active compounds of the present invention are also suitable for controlling arthropods, helminths and protozoas which attack an animal. The animal includes an agricultural livestock like a cow, a sheep, a goat, a horse, a pig, a donkey, a camel, a buffalo, a rabbit, a chicken, a turkey, a duck, a goose, a nursery fish, a honey bee and the like. In addition, the animal also includes a pet (i.e., companion animal) like a dog, a cat, a pet bird, an aquarium fish and the like and an animal known as a test animal like a hamster, a guinea pig, a rat, a mouse and the like.

With the control of these arthropods, helminths and/or protozoas by using the active compounds of the present invention, death ratio of the host animal is reduced, productivity (for obtaining meat, milk, wool, leather, eggs and honey, etc.) and health of the host animal are expected to be improved, and also economically more favorable and convenient breeding of the animal can be achieved.

For example, (when applicable) it is preferable that blood mixing from a host via parasites is inhibited or interrupted. In addition, control of parasite can be useful for inhibiting transfer of infectious factors.

The term "control" used in the present specification in relation to a veterinary field means that the active compounds of the present invention are effective for reducing the occurrence of parasites in the animal infected with each parasite to a harmless level. More specifically, the term "control" used in the present specification means that the active compounds of the present invention are effective for eradicating each parasite or for inhibiting its growth or proliferation.

In general, when used for an animal treatment, the compounds of the present invention can be directly applied. Preferably, the compounds of the present invention are applied as pharmaceutical compositions which may contain vehicles and/or auxiliary agents that are known in the field and pharmaceutically acceptable.

In a veterinary medicine field and livestock farming, the active compounds can be applied (administered) in various known ways, such as via enteral administration in form of a tablet, a capsule, a drink, a syrup, a granule, a paste, a bolus and a feed stuff, or a suppository; via parenteral administration based on injection (intramuscular, subcutaneous, intravenous, intraperitoneal, etc.), implant, intranasal administration, etc.; by administration on skin in form of impregnation, liquid impregnation, spray, pouring on, spotting on, washing and powder spray; or with an aid of an molded article containing the active compounds, such as a neck tag, an ear tag, a tail tag, a leg tag, a horse rein, an identification tag, etc. The active compounds also can be prepared as shampoo, an appropriate preparation usable in aerosol, or as an unpressurized spray, for example a pump spray and a sprayer.

When used for livestock, poultry, pet and the like, the active compounds of the present invention can be prepared as a formulation containing them in an amount of 1 to 80% of weight (for example, powder, wettable preparation (WP), an emulsion, an emulsified concentrate (EC), a flowable, a homogenous solution and a suspension concentrate (SC)), and then can be applied directly or after dilution (for example, 100 to 10,000 times dilution), or they can be also applied as impregnation solution.

When used in a field of veterinary medicine, the active compounds of the present invention can be used in combination with appropriate synergists such as acaricides, pesticides, anti-helminth agents or anti-protozoa agents or with other active compounds.

In the present invention, the compounds which have a pesticidal activity against the harmful pests encompassing all of above are also referred to as insecticides.

When used as insecticides, the active compounds of the present invention can be prepared in a common preparation form. Such a preparation form may include, for example, a solution, an emulsion, wettable powder, granulated wettable powder, a suspension, powder, a foam, a paste, a tablet, a granule, an aerosol, a natural or synthetic agent impregnated with the active compounds, a microcapsule, a coating agent for seeds, a formulation equipped with a combustion device (the combustion device can be a smoke or fog cartridge, a can or a coil, etc.) and ULV (cold mist, warm mist), and the like. These formulations may be prepared by methods known per se. For example, they can be prepared by mixing the active compounds together with spreading agents, i.e. liquid diluents or carriers; liquefied gas diluents or carriers; solid diluents or carriers, and, optionally, with surfactants i.e. emulsifiers and/or dispersants and/or foam-forming agents.

When water is used as a spreading agent, for example, organic solvents may be used as auxiliary solvents. The liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes) or paraffins (e.g. mineral oil fractions), alcohols (e.g. butanol, glycol and ethers or esters thereof, etc.), ketones (e.g. acetone, methyl ethyl ketone, methyl isobutyl ketone, cyclohexanone etc.), strong polar solvents (e.g. dimethylformamide, dimethylsulfoxide etc.), water and the like. The liquefied gas dilution agents or carriers may include those present as gas at atmospheric temperature and by evaporation, for example, butane, propane, nitrogen gas, carbon dioxide, and an aerosol propellant such as halogenated hydrocarbons. Examples of the solid dilution agents include ground natural minerals (for example, kaolins, clay, talc, chalk, quartz, attapulgite, montmorillonite, diatomaceous earth, etc.) and finely-ground synthetic minerals (for example, highly dispersed silicic acid, alumina and silicate, etc.) and the like. Examples of the solid carriers for granules may include finely pulverized and sifted rocks (for example, calcite, marble, pumice, sepiolite and dolomite, etc.), synthetic granules of inorganic or organic powders, and fine granules of organic materials (for example, sawdust, coconut shells, corn cobs and tobacco stalks, etc.) and the like. Examples of the emulsifiers and/or foam formers may include nonionic and anionic emulsifiers, for example, polyoxyethylene fatty acid esters, polyoxyethylene fatty acid alcohol ethers (for example, alkylaryl polyglycol ether), alkyl sulfonates, alkyl sulfates and aryl sulfonates, and albumin hydrolysates and the like. Examples of the dispersants include lignin sulfite waste liquor and methylcellulose. Binders may also be used in the formulation (powder, granule and emulsion). Examples of the binders may include carboxymethyl cellulose, natural or synthetic polymers (for example, gum arabic, polyvinyl alcohol and polyvinyl acetate, etc.). Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc. In general, the formulation may include the above active components in an amount of 0.1 to 95% by weight, preferably 0.5 to 90% by weight.

The active compounds represented by the formula (I) of the present invention can be provided as mixtures with other active compounds such as pesticides, poison baits, sterilizing agents, acaricidal agents, nematocides, fungicides, growth regulating agents, and herbicides in a form of commercially useful formulation or an application form modified from formulation thereof. Herein, examples of the insecticide include organic phosphorus agents, carbamate agents, carboxylate agents, chlorinated hydrocarbon agents, neonicotinoide insecticides and insecticidal substances produced from organisms.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

(1) Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, and Vamidothion.

(2) GABA-gated chloride channel antagonists, for example cyclodiene organochlorines, e.g. Chlordane and Endosulfan; or phenylpyrazoles (fiproles), e.g. Ethiprole and Fipronil.

(3) Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin[(1R)-trans isomers], Deltamethrin, Empenthrin[(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin[(1R)-trans isomer), Prallethrin, Pyrethrine (pyrethrum), Resmethrin, Silafluofen, Tefluthrin, Tetramethrin, Tetramethrin[(1R) isomers)], Tralomethrin, and Transfluthrin; or DDT; or Methoxychlor.

(4) Nicotinic acetylcholine receptor (nAChR) agonists, for example neonicotinoids, e.g. Acetamiprid, Clothianidin, Dinotefuran, Imidacloprid, Nitenpyram, Thiacloprid, and Thiamethoxam; or Nicotine.

(5) Nicotinic acetylcholine receptor (nAChR) allosteric activators, for example spinosyns, e.g. Spinetoram and Spinosad.

(6) Chloride channel activators, for example avermectins/milbemycins, e.g. Abamectin, Emamectin benzoate, Lepimectin, and Milbemectin.

(7) Juvenile hormone mimics, for example juvenile hormon analogues, e.g. Hydroprene, Kinoprene, and Methoprene; or Fenoxycarb; or Pyriproxyfen.

(8) Miscellaneous non-specific (multi-site) inhibitors, for example alkyl halides, e.g. Methyl bromide and other alkyl halides; or Chloropicrin; or Sulfuryl fluoride; or Borax; or Tartar emetic.

(9) Selective homopteran feeding blockers, e.g. Pymetrozine; or Flonicamid.

(10) Mite growth inhibitors, e.g. Clofentezine, Hexythiazox, and Diflovidazin; or Etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example Diafenthiuron; or organotin miticides, e.g. Azocyclotin, Cyhexatin, and Fenbutatin oxide; or Propargite; or Tetradifon.

(13) Uncouplers of oxidative phoshorylation via disruption of the proton gradient, for example Chlorfenapyr, DNOC, and Sulfluramid.

(14) Nicotinic acetylcholine receptor (nAChR) channel blockers, for example Bensultap, Cartap hydrochloride, Thiocyclam, and Thiosultap-sodium.

(15) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide, and Tebufenozide.

(19) Octopamine receptor agonists, for example Amitraz.

(20) Mitochondrial complex III electron transport inhibitors, for example Hydramethylnon; or Acequinocyl; or Fluacrypyrim.

(21) Mitochondrial complex I electron transport inhibitors, for example METI acaricides, e.g. Fenazaquin, Fenpyroximate, Pyrimidifen, Pyridaben, Tebufenpyrad, and Tolfenpyrad; or Rotenone (Derris).

(22) Voltage-dependent sodium channel blockers, e.g. Indoxacarb; or Metaflumizone.

(23) Inhibitors of acetyl CoA carboxylase, for example tetronic and tetramic acid derivatives, e.g. Spirodiclofen, Spiromesifen, and Spirotetramat.

(24) Mitochondrial complex IV electron transport inhibitors, for example phosphines, e.g. Aluminium phosphide, Calcium phosphide, Phosphine, and Zinc phosphide; or Cyanide.

(25) Mitochondrial complex II electron transport inhibitors, for example Cyenopyrafen.

(28) Ryanodine receptor modulators, for example diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl](cyclopropyl)amino}furan-2(5H)-one (known from WO2007/115643), 4-{[(6-chloropyridin-3-yl)methyl](cyclopropyl)amino}furan-2(5H)-one (known from EP-A-0 539 588), 4-{[(6-chlorpyridin-3-yl)methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (also known from WO2007/149134) as well as Sulfoxaflor and its diastereomers[(R)-methyl(oxido){(1R)-1-[6-(trifluoromethyl)pyridin-3-yl]ethyl}-$\lambda^4$-sulfanylidene]cyanamide (A1) and [(S)-methyl(oxido) {(1S)-1-[6-(trifluoromethyl)pyridin-3-yl]ethyl}-$\lambda^4$-sulfanylidene] cyanamide (A2), referred to as group of diastereomers A (known from WO2010/074747, WO2010/074751), [(R)-methyl(oxido) {(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl) sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy)-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazine-carboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-1 [5-(trifluoromethyl)-1H-tetrazol-1-yl]methyl 1-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

Fungicides which can be used in a combination according to the invention are the following:

(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]-phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methano naphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4]triazolo[1,5-a]pyrimidine and 3-chloro-5-(6-chloropyridin-3-yl)-6-methyl-4-(2,4,6-trifluorophenyl)pyridazine.

(5) Compounds capable to have a multisite action, for example bordeaux mixture, captafol, captan, chlorothalonil, copper hydroxide, copper naphthenate, copper oxide, copper oxychloride, copper (2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(6) Compounds capable to induce a host defence, for example acibenzolar-S-methyl, isotianil, probenazole and tiadinil.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon, tricyclazole and 2,2,2-trifluoroethyl {3-methyl-1-[(4-methylbenzoyl)amino]butan-2-yl}carbamate.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propano sine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanide, triazoxide, trichlamide, zarilamid, (3S,6S,7R,8R)-8-benzyl-3-[({3-[(isobutyryloxy)methoxyl]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoro-methyl)-1H-pyrazol-1-yl]ethanone, 1-(4-{4-[(5S)-5-(2,6-difluorophenyl)-4,5-dihydro-1,2-oxazol-3-yl]-1,3-thiazol-2- yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfono-hydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All named mixing partners of the classes (1) to (16) can, if their functional groups enable this, optionally form salts with suitable bases or acids.

Herbicidal components which can be used in combination with the active compounds according to the invention in mixed formulations or in tank mix are, for example, known active compounds as they are described in, for example, Weed Research 26, 441-445 (1986), or "The Pesticide Manual", 15th edition, The British Crop Protection Council and the Royal Soc. of Chemistry, 2006, and the literature cited therein, and which for example act as inhibitor of acetolactate synthase, acetyl-CoA-carboxylase, cellulose-synthase, enolpyruvylshikimat-3-phosphat-synthase, glutamin-synthetase, p-hydroxyphenylpyruvat-dioxygenase, phytoendesaturase, photosystem I, photosystem II and/or protoporphyrinogen-oxidase.

Examples of active compounds which may be mentioned as herbicides or plant growth regulators which are known from the literature and which can be combined with the compounds according to the invention are the following (compounds are either described by "common name" in accordance with the International Organization for Standardization (ISO) or by chemical name or by a customary code number), and always comprise all applicable forms such as acids, salts, ester, or modifications such as isomers, like stereoisomers and optical isomers. As an example at least one applicable from and/or modifications can be mentioned:
acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-methyl, aminocyclopyrachlor-potassium, aminopyralid, amitrole, ammoniumsulfamat, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chlorid, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]-ethansulfonamide, F-7967, i.e. 3-[7-chloro-5-fluoro-2-(trifluoromethyl)-1H-benzimidazol-4-yl]-1-methyl-6-(trifluoromethyl)pyrimidin-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellinic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl)-O-ethyl-isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxypho sphoryl)-ethyl-(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indol-3-ylacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl, and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chlorid, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropen, methylisothiocyanat, metobenzuron, metobromuron, metolachlor, S-metolachlor, metosulam, metoxuron, metribuzin, metsulfuron, metsulfuron-methyl, molinate, monalide, monocarbamide, monocarbamide-dihydrogensulphate, monolinuron, monosulfuron, monosulfuron ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (mixture of isomers), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl-(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl-5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidin-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, as well as the following compounds:

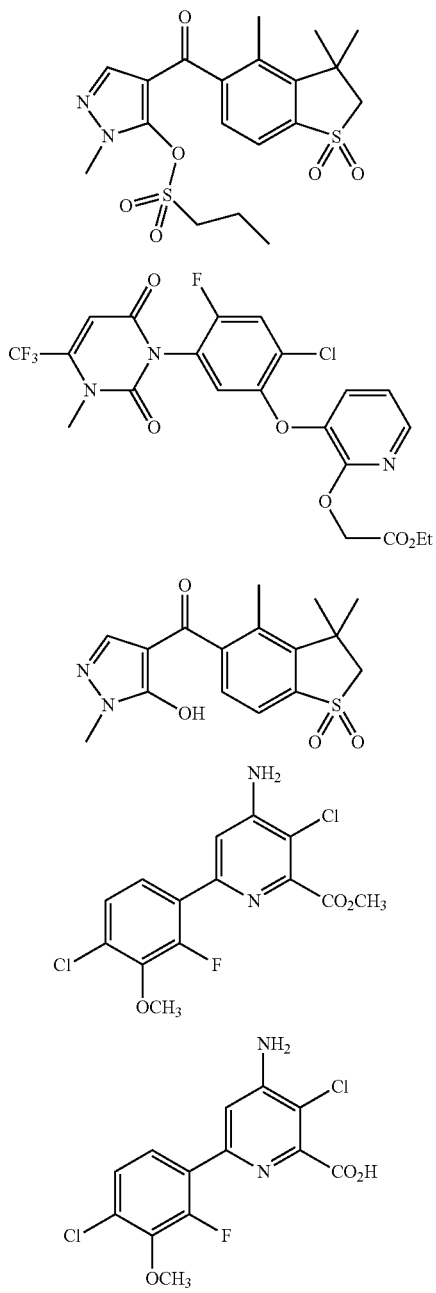

-continued

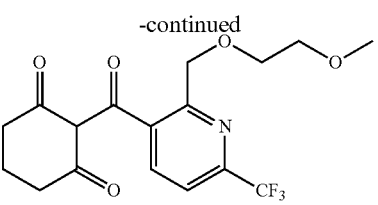

Further, the active compounds of formula (I) of the present invention can be present in a formulation or use form as a mixed agent with synergists. Examples of the formulation or use form are those commercially useful. The synergists per se need not be active but can enhance the activity of the active compounds. The amount of the compounds of the present invention in commercially useful application form may vary over a broad range. The concentration of the active compounds of the formula (I) of the present invention for actual use may be, for example, between 0.0000001 and 100% by weight, preferably between 0.00001 and 1% by weight. The compounds of the formula (I) of the present invention can be used according to any common methods suitable for each application form.

Additionally to above mentioned, the present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

The active compounds of the present invention have stability that is effective for alkaline substances present on lime materials when the compounds are used against hygienic pests and other stored product pests. In addition, they exhibit excellent residual effectiveness on woods and soils.

In general, when used for an animal treatment, the compounds of the present invention can be directly applied. Preferably, the compounds of the present invention are applied as pharmaceutical compositions which may contain vehicles and/or auxiliary agents that are known in the field and pharmaceutically acceptable.

In a veterinary medicine field and livestock farming, the active compounds can be applied (administered) in various known ways, such as via enteral administration in form of a tablet, a capsule, a drink, a syrup, a granule, a paste, a bolus and a feed stuff, or a suppository; via parenteral administration based on injection (intramuscular, subcutaneous, intravenous, intraperitoneal, etc.), implant, intranasal administration, etc.; by administration on skin in form of impregnation, liquid impregnation, spray, pouring on, spotting on, washing and powder spray; or with an aid of an molded article containing the active compounds, such as a neck tag, an ear tag, a tail tag, a leg tag, a horse rein, an identification tag, etc. The active compounds also can be prepared as shampoo, an appropriate preparation usable in aerosol, or as an unpressurized spray, for example a pump spray and a sprayer.

When used for livestock, poultry, pet and the like, the active compounds of the present invention can be prepared as a formulation containing them in an amount of 1 to 80% of weight [for example, powder, wettable preparation (WP), an emulsion, an emulsified concentrate (EC), a flowable, a homogenous solution and a suspension concentrate (SC)], and then can be applied directly or after dilution (for example, 100 to 10,000 times dilution), or they can be also applied as impregnation solution.

When used in a field of veterinary medicine, the active compounds of the present invention can be used in combination with appropriate synergists or other active compounds such as acaricides, pesticides, anti-helminth agents or anti-protozoa agents.

The compounds of the present invention have low toxicity against worm-blooded animals, and therefore can be used safely.

Herein below, the present invention will be exemplified by the following examples. However, the present invention should not be construed as being limit to these examples.

PREPARATION EXAMPLES

Compounds according to the invention which have been or can be prepared according to the invention as well as their intermediates are exemplified in the following tables.

Synthesis of N-(5-{3-[3,5-bis(trifluoromethyl)phenyl]-2-hydroxy-3-(trifluoromethyl)pyrrolidin-1-yl}-2,3-dihydro-1H-inden-1-yl)propanamide, Ex. No. (I-A-38)

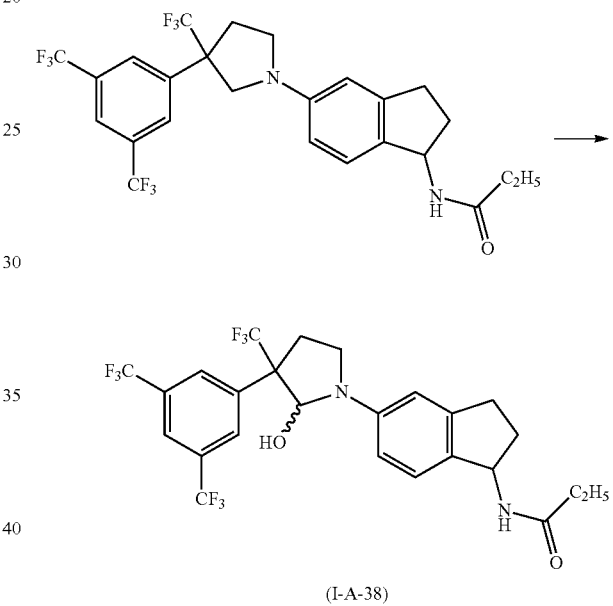

(I-A-38)

131 mg (0.243 mmole) N-(5-{3-[3,5-bis(trifluoromethyl)phenyl]-3-(trifluoromethyl)pyrrolidin-1-yl}-2,3-dihydro-1H-inden-1-yl)propanamide (Ex. No. (II-a-963), known from WO 2010/043315, Table 6, Ex. No. 273) was dissolved in a solution of 0.6 ml water, 6 ml acetonitrile and 1.2 ml trifluoroacetic acid. At 0° C. 86 mg (0.243 mmole) silver-(II) 2-pyridinecarboxylate were added in small portions until the solution has been discoloured. Immediately after decolourization ethylacetate and sodium hydrogencarbonate solution were added. The aqueous solution was extracted additionally two times with ethylacetate. The combined extracts were dried and evaporated under reduced pressure. The residue was purified by a reversed phase chromatography with a gradient acetonitrile/water to obtain 9 mg (5.8%) of the title compound as a mixture of isomers. NMR data are given for the main isomer.

$^1$H-NMR: see the table below

Analogously the following compounds of formula (I-A) can be prepared ($R^1$=$CF_3$; W=O, $B^1$=$B^3$=$B^4$=CH, $R^3$=H, $R^{6'}$=H, E=$CH_2$):

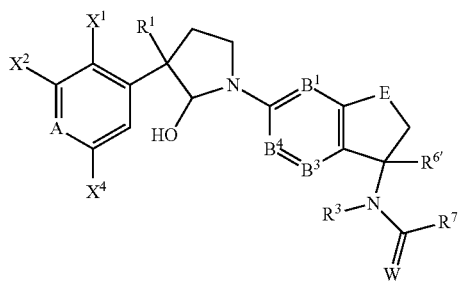

(I-A)

Abbreviations which are used in the tables include the following:

nPr = CH₂—CH₂—CH₃
iPr = isopropyl = CH(CH₃)₂

nBu = CH₂—CH₂—CH₂—CH₃
iBu = CH₂—CH(CH₃)₂

TABLE 1

| Ex. No. | X¹ | X² | A | X⁴ | R⁷ |
|---|---|---|---|---|---|
| I-A-1 | H | Cl | CH | Cl | CH₃ |
| I-A-2 | H | Cl | CH | Cl | CH₂CH₃ |
| I-A-3 | H | Cl | CH | Cl | CH₂CF₃ |
| I-A-4 | H | Cl | CH | Cl | CH₂CH₂CH₃ |
| I-A-5 | H | Cl | CH | Cl | iPr |
| I-A-6 | H | Cl | CH | Cl | iBu |
| I-A-7 | H | Cl | CH | Cl | cPr |
| I-A-8 | H | Cl | CH | Cl | cBu |
| I-A-9 | H | Cl | CH | Cl | CH₂cPr |
| I-A-10 | H | Cl | CH | Cl | CH₂SCH₃ |
| I-A-11 | H | Cl | CH | Cl | CH₂SOCH₃ |
| I-A-12 | H | Cl | CH | Cl | CH₂SO₂CH₃ |
| I-A-13 | H | Cl | CCl | Cl | CH₃ |
| I-A-14 | H | Cl | CCl | Cl | CH₂CH₃ |
| I-A-15 | H | Cl | CCl | Cl | CH₂CF₃ |
| I-A-16 | H | Cl | CCl | Cl | CH₂CH₂CH₃ |
| I-A-17 | H | Cl | CCl | Cl | iPr |
| I-A-18 | H | Cl | CCl | Cl | iBu |
| I-A-19 | H | Cl | CCl | Cl | cPr |
| I-A-20 | H | Cl | CCl | Cl | cBu |
| I-A-21 | H | Cl | CCl | Cl | CH₂cPr |
| I-A-22 | H | Cl | CCl | Cl | CH₂SCH₃ |
| I-A-23 | H | Cl | CCl | Cl | CH₂SOCH₃ |
| I-A-24 | H | Cl | CCl | Cl | CH₂SO₂CH₃ |
| I-A-25 | F | Cl | CF | Cl | CH₃ |
| I-A-26 | F | Cl | CF | Cl | CH₂CH₃ |
| I-A-27 | F | Cl | CF | Cl | CH₂CF₃ |
| I-A-28 | F | Cl | CF | Cl | CH₂CH₂CH₃ |
| I-A-29 | F | Cl | CF | Cl | iPr |
| I-A-30 | F | Cl | CF | Cl | iBu |
| I-A-31 | F | Cl | CF | Cl | cPr |
| I-A-32 | F | Cl | CF | Cl | cBu |
| I-A-33 | F | Cl | CF | Cl | CH₂cPr |
| I-A-34 | F | Cl | CF | Cl | CH₂SCH₃ |
| I-A-35 | F | Cl | CF | Cl | CH₂SOCH₃ |
| I-A-36 | F | Cl | CF | Cl | CH₂SO₂CH₃ |
| I-A-37 | H | CF₃ | CH | CF₃ | CH₃ |
| I-A-38 | H | CF₃ | CH | CF₃ | CH₂CH₃ |
| I-A-39 | H | CF₃ | CH | CF₃ | CH₂CF₃ |
| I-A-40 | H | CF₃ | CH | CF₃ | CH₂CH₂CH₃ |
| I-A-41 | H | CF₃ | CH | CF₃ | iPr |

TABLE 1-continued

| Ex. No. | X¹ | X² | A | X⁴ | R⁷ |
|---|---|---|---|---|---|
| I-A-42 | H | CF₃ | CH | CF₃ | iBu |
| I-A-43 | H | CF₃ | CH | CF₃ | cPr |
| I-A-44 | H | CF₃ | CH | CF₃ | cBu |
| I-A-45 | H | CF₃ | CH | CF₃ | CH₂cPr |
| I-A-46 | H | CF₃ | CH | CF₃ | CH₂SCH₃ |
| I-A-47 | H | CF₃ | CH | CF₃ | CH₂SOCH₃ |
| I-A-48 | H | CF₃ | CH | CF₃ | CH₂SO₂CH₃ |
| I-A-49 | H | Cl | CF | Cl | CH₃ |
| I-A-50 | H | Cl | CF | Cl | CH₂CH₃ |
| I-A-51 | H | Cl | CF | Cl | CH₂CF₃ |
| I-A-52 | H | Cl | CF | Cl | CH₂CH₂CH₃ |
| I-A-53 | H | Cl | CF | Cl | iPr |
| I-A-54 | H | Cl | CF | Cl | iBu |
| I-A-55 | H | Cl | CF | Cl | cPr |
| I-A-56 | H | Cl | CF | Cl | cBu |
| I-A-57 | H | Cl | CF | Cl | CH₂cPr |
| I-A-58 | H | Cl | CF | Cl | CH₂SCH₃ |
| I-A-59 | H | Cl | CF | Cl | CH₂SOCH₃ |
| I-A-60 | H | Cl | CF | Cl | CH₂SO₂CH₃ |
| I-A-61 | H | Cl | CBr | Cl | CH₃ |
| I-A-62 | H | Cl | CBr | Cl | CH₂CH₃ |
| I-A-63 | H | Cl | CBr | Cl | CH₂CF₃ |
| I-A-64 | H | Cl | CBr | Cl | CH₂CH₂CH₃ |
| I-A-65 | H | Cl | CBr | Cl | iPr |
| I-A-66 | H | Cl | CBr | Cl | iBu |
| I-A-67 | H | Cl | CBr | Cl | cPr |
| I-A-68 | H | Cl | CBr | Cl | cBu |
| I-A-69 | H | Cl | CBr | Cl | CH₂cPr |
| I-A-70 | H | Cl | CBr | Cl | CH₂SCH₃ |
| I-A-71 | H | Cl | CBr | Cl | CH₂SOCH₃ |
| I-A-72 | H | Cl | CBr | Cl | CH₂SO₂CH₃ |
| I-A-73 | H | Cl | CH | CF₃ | CH₃ |
| I-A-74 | H | Cl | CH | CF₃ | CH₂CH₃ |
| I-A-75 | H | Cl | CH | CF₃ | CH₂CF₃ |
| I-A-76 | H | Cl | CH | CF₃ | CH₂CH₂CH₃ |
| I-A-77 | H | Cl | CH | CF₃ | iPr |
| I-A-78 | H | Cl | CH | CF₃ | iBu |
| I-A-79 | H | Cl | CH | CF₃ | cPr |
| I-A-80 | H | Cl | CH | CF₃ | cBu |
| I-A-81 | H | Cl | CH | CF₃ | CH₂cPr |
| I-A-82 | H | Cl | CH | CF₃ | CH₂SCH₃ |
| I-A-83 | H | Cl | CH | CF₃ | CH₂SOCH₃ |
| I-A-84 | H | Cl | CH | CF₃ | CH₂SO₂CH₃ |
| I-A-85 | H | Cl | CCl | CF₃ | CH₃ |
| I-A-86 | H | Cl | CCl | CF₃ | CH₂CH₃ |
| I-A-87 | H | Cl | CCl | CF₃ | CH₂CF₃ |
| I-A-88 | H | Cl | CCl | CF₃ | CH₂CH₂CH₃ |
| I-A-89 | H | Cl | CCl | CF₃ | iPr |
| I-A-90 | H | Cl | CCl | CF₃ | iBu |
| I-A-91 | H | Cl | CCl | CF₃ | cPr |
| I-A-92 | H | Cl | CCl | CF₃ | cBu |
| I-A-93 | H | Cl | CCl | CF₃ | CH₂cPr |
| I-A-94 | H | Cl | CCl | CF₃ | CH₂SCH₃ |
| I-A-95 | H | Cl | CCl | CF₃ | CH₂SOCH₃ |
| I-A-96 | H | Cl | CCl | CF₃ | CH₂SO₂CH₃ |
| I-A-97 | F | Cl | CCl | Cl | CH₃ |
| I-A-98 | F | Cl | CCl | Cl | CH₂CH₃ |
| I-A-99 | F | Cl | CCl | Cl | CH₂CF₃ |
| I-A-100 | F | Cl | CCl | Cl | CH₂CH₂CH₃ |
| I-A-101 | F | Cl | CCl | Cl | iPr |
| I-A-102 | F | Cl | CCl | Cl | iBu |
| I-A-103 | F | Cl | CCl | Cl | cPr |
| I-A-104 | F | Cl | CCl | Cl | cBu |
| I-A-105 | F | Cl | CCl | Cl | CH₂cPr |
| I-A-106 | F | Cl | CCl | Cl | CH₂SCH₃ |
| I-A-107 | F | Cl | CCl | Cl | CH₂SOCH₃ |
| I-A-108 | F | Cl | CCl | Cl | CH₂SO₂CH₃ |
| I-A-109 | H | CF₃ | CF | H | CH₃ |
| I-A-110 | H | CF₃ | CF | H | CH₂CH₃ |
| I-A-111 | H | CF₃ | CF | H | CH₂CF₃ |
| I-A-112 | H | CF₃ | CF | H | CH₂CH₂CH₃ |
| I-A-113 | H | CF₃ | CF | H | iPr |
| I-A-114 | H | CF₃ | CF | H | iBu |
| I-A-115 | H | CF₃ | CF | H | cPr |
| I-A-116 | H | CF₃ | CF | H | cBu |
| I-A-117 | H | CF₃ | CF | H | CH₂cPr |
| I-A-118 | H | CF₃ | CF | H | CH₂SCH₃ |
| I-A-119 | H | CF₃ | CF | H | CH₂SOCH₃ |

TABLE 1-continued

| Ex. No. | X¹ | X² | A | X⁴ | R⁷ |
|---|---|---|---|---|---|
| I-A-120 | H | CF₃ | CF | H | CH₂SO₂CH₃ |
| I-A-121 | H | Cl | CCl | H | CH₃ |
| I-A-122 | H | Cl | CCl | H | CH₂CH₃ |
| I-A-123 | H | Cl | CCl | H | CH₂CF₃ |
| I-A-124 | H | Cl | CCl | H | CH₂CH₂CH₃ |
| I-A-125 | H | Cl | CCl | H | iPr |
| I-A-126 | H | Cl | CCl | H | iBu |
| I-A-127 | H | Cl | CCl | H | cPr |
| I-A-128 | H | Cl | CCl | H | cBu |
| I-A-129 | H | Cl | CCl | H | CH₂cPr |
| I-A-130 | H | Cl | CCl | H | CH₂SCH₃ |
| I-A-131 | H | Cl | CCl | H | CH₂SOCH₃ |
| I-A-132 | H | Cl | CCl | H | CH₂SO₂CH₃ |
| I-A-133 | H | Cl | CH | H | CH₃ |
| I-A-134 | H | Cl | CH | H | CH₂CH₃ |
| I-A-135 | H | Cl | CH | H | CH₂CF₃ |
| I-A-136 | H | Cl | CH | H | CH₂CH₂CH₃ |
| I-A-137 | H | Cl | CH | H | iPr |
| I-A-138 | H | Cl | CH | H | iBu |
| I-A-139 | H | Cl | CH | H | cPr |
| I-A-140 | H | Cl | CH | H | cBu |
| I-A-141 | H | Cl | CH | H | CH₂cPr |
| I-A-142 | H | Cl | CH | H | CH₂SCH₃ |
| I-A-143 | H | Cl | CH | H | CH₂SOCH₃ |
| I-A-144 | H | Cl | CH | H | CH₂SO₂CH₃ |

Synthesis of N-{5-[3-(3,5-dichlorophenyl)-2-oxo-3-(trifluoromethyl)pyrrolidin-1-yl]-2,3-dihydro-1H-inden-1-yl}propanamide, Ex. No. (I-B-2)

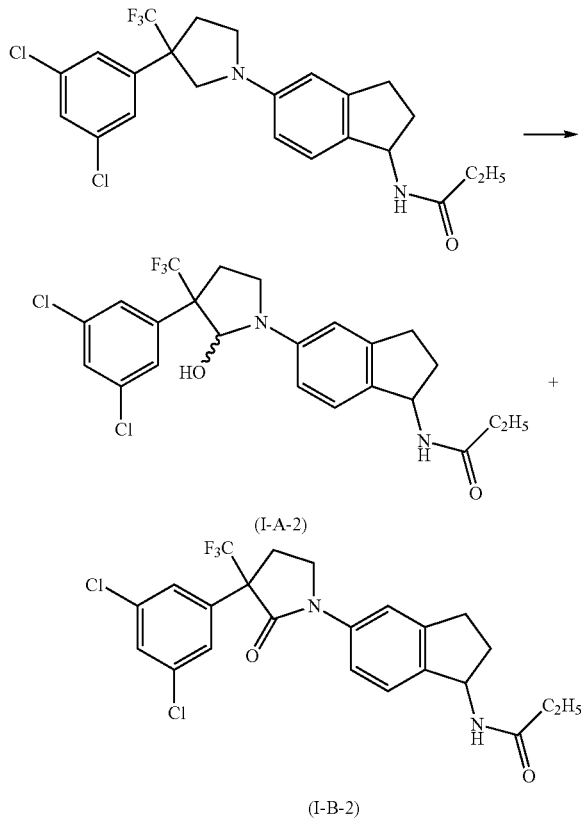

(I-B-2)

To a solution of 235.7 mg N-{5-[3-(3,5-dichlorophenyl)-3-(trifluoromethyl)pyrrolidin-1-yl]-2,3-dihydro-1H-inden-1-yl}propanamide (0.5 mmol) in 20 ml toluene was added 1304 mg manganese(IV)dioxide (15.0 mmol) and stirred at 20° C. for 12 h. After standing for about 2 d at room temperature 100 µl acetic acid were added and the mixture stirred for 15.5 h. The reaction mixture was filtered through celite-silica gel. The crude product (198 mg) was subjected to silica gel column chromatography yielding 20 mg of compound (I-A-2) and 67 mg pure N-{5-[3-(3,5-dichlorophenyl)-2-oxo-3-(trifluoromethyl)pyrrolidin-1-yl]-2,3-dihydro-1H-inden-1-yl}propanamide (I-B-2).

¹H-NMR: see the table below

By the same method the following compounds of formula (I-B) can be prepared (R¹=CF₃; W=O, B¹=B³=B⁴=CH, R³=H, R⁶'=H, E=CH₂):

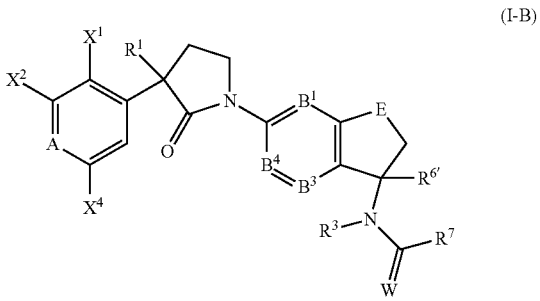

(I-B)

TABLE 2

| Ex. No. | X¹ | X² | A | X⁴ | R⁷ |
|---|---|---|---|---|---|
| I-B-1 | H | Cl | CH | Cl | CH₃ |
| I-B-2 | H | Cl | CH | Cl | CH₂CH₃ |
| I-B-3 | H | Cl | CH | Cl | CH₂CF₃ |
| I-B-4 | H | Cl | CH | Cl | CH₂CH₂CH₃ |
| I-B-5 | H | Cl | CH | Cl | iPr |
| I-B-6 | H | Cl | CH | Cl | iBu |
| I-B-7 | H | Cl | CH | Cl | cPr |
| I-B-8 | H | Cl | CH | Cl | cBu |
| I-B-9 | H | Cl | CH | Cl | CH₂cPr |
| I-B-10 | H | Cl | CH | Cl | CH₂SCH₃ |
| I-B-11 | H | Cl | CH | Cl | CH₂SOCH₃ |
| I-B-12 | H | Cl | CH | Cl | CH₂SO₂CH₃ |
| I-B-13 | H | Cl | CCl | Cl | CH₃ |
| I-B-14 | H | Cl | CCl | Cl | CH₂CH₃ |
| I-B-15 | H | Cl | CCl | Cl | CH₂CF₃ |
| I-B-16 | H | Cl | CCl | Cl | CH₂CH₂CH₃ |
| I-B-17 | H | Cl | CCl | Cl | iPr |
| I-B-18 | H | Cl | CCl | Cl | iBu |
| I-B-19 | H | Cl | CCl | Cl | cPr |
| I-B-20 | H | Cl | CCl | Cl | cBu |
| I-B-21 | H | Cl | CCl | Cl | CH₂cPr |
| I-B-22 | H | Cl | CCl | Cl | CH₂SCH₃ |
| I-B-23 | H | Cl | CCl | Cl | CH₂SOCH₃ |
| I-B-24 | H | Cl | CCl | Cl | CH₂SO₂CH₃ |
| I-B-25 | F | Cl | CF | Cl | CH₃ |
| I-B-26 | F | Cl | CF | Cl | CH₂CH₃ |
| I-B-27 | F | Cl | CF | Cl | CH₂CF₃ |
| I-B-28 | F | Cl | CF | Cl | CH₂CH₂CH₃ |
| I-B-29 | F | Cl | CF | Cl | iPr |
| I-B-30 | F | Cl | CF | Cl | iBu |
| I-B-31 | F | Cl | CF | Cl | cPr |
| I-B-32 | F | Cl | CF | Cl | cBu |
| I-B-33 | F | Cl | CF | Cl | CH₂cPr |
| I-B-34 | F | Cl | CF | Cl | CH₂SCH₃ |
| I-B-35 | F | Cl | CF | Cl | CH₂SOCH₃ |
| I-B-36 | F | Cl | CF | Cl | CH₂SO₂CH₃ |
| I-B-37 | H | CF₃ | CH | CF₃ | CH₃ |
| I-B-38 | H | CF₃ | CH | CF₃ | CH₂CH₃ |
| I-B-39 | H | CF₃ | CH | CF₃ | CH₂CF₃ |
| I-B-40 | H | CF₃ | CH | CF₃ | CH₂CH₂CH₃ |
| I-B-41 | H | CF₃ | CH | CF₃ | iPr |
| I-B-42 | H | CF₃ | CH | CF₃ | iBu |

TABLE 2-continued

| Ex. No. | X$^1$ | X$^2$ | A | X$^4$ | R$^7$ |
|---|---|---|---|---|---|
| I-B-43 | H | CF$_3$ | CH | CF$_3$ | cPr |
| I-B-44 | H | CF$_3$ | CH | CF$_3$ | cBu |
| I-B-45 | H | CF$_3$ | CH | CF$_3$ | CH$_2$cPr |
| I-B-46 | H | CF$_3$ | CH | CF$_3$ | CH$_2$SCH$_3$ |
| I-B-47 | H | CF$_3$ | CH | CF$_3$ | CH$_2$SOCH$_3$ |
| I-B-48 | H | CF$_3$ | CH | CF$_3$ | CH$_2$SO$_2$CH$_3$ |
| I-B-49 | H | Cl | CF | Cl | CH$_3$ |
| I-B-50 | H | Cl | CF | Cl | CH$_2$CH$_3$ |
| I-B-51 | H | Cl | CF | Cl | CH$_2$CF$_3$ |
| I-B-52 | H | Cl | CF | Cl | CH$_2$CH$_2$CH$_3$ |
| I-B-53 | H | Cl | CF | Cl | iPr |
| I-B-54 | H | Cl | CF | Cl | iBu |
| I-B-55 | H | Cl | CF | Cl | cPr |
| I-B-56 | H | Cl | CF | Cl | cBu |
| I-B-57 | H | Cl | CF | Cl | CH$_2$cPr |
| I-B-58 | H | Cl | CF | Cl | CH$_2$SCH$_3$ |
| I-B-59 | H | Cl | CF | Cl | CH$_2$SOCH$_3$ |
| I-B-60 | H | Cl | CF | Cl | CH$_2$SO$_2$CH$_3$ |
| I-B-61 | H | Cl | CBr | Cl | CH$_3$ |
| I-B-62 | H | Cl | CBr | Cl | CH$_2$CH$_3$ |
| I-B-63 | H | Cl | CBr | Cl | CH$_2$CF$_3$ |
| I-B-64 | H | Cl | CBr | Cl | CH$_2$CH$_2$CH$_3$ |
| I-B-65 | H | Cl | CBr | Cl | iPr |
| I-B-66 | H | Cl | CBr | Cl | iBu |
| I-B-67 | H | Cl | CBr | Cl | cPr |
| I-B-68 | H | Cl | CBr | Cl | cBu |
| I-B-69 | H | Cl | CBr | Cl | CH$_2$cPr |
| I-B-70 | H | Cl | CBr | Cl | CH$_2$SCH$_3$ |
| I-B-71 | H | Cl | CBr | Cl | CH$_2$SOCH$_3$ |
| I-B-72 | H | Cl | CBr | Cl | CH$_2$SO$_2$CH$_3$ |
| I-B-73 | H | Cl | CH | CF$_3$ | CH$_3$ |
| I-B-74 | H | Cl | CH | CF$_3$ | CH$_2$CH$_3$ |
| I-B-75 | H | Cl | CH | CF$_3$ | CH$_2$CF$_3$ |
| I-B-76 | H | Cl | CH | CF$_3$ | CH$_2$CH$_2$CH$_3$ |
| I-B-77 | H | Cl | CH | CF$_3$ | iPr |
| I-B-78 | H | Cl | CH | CF$_3$ | iBu |
| I-B-79 | H | Cl | CH | CF$_3$ | cPr |
| I-B-80 | H | Cl | CH | CF$_3$ | cBu |
| I-B-81 | H | Cl | CH | CF$_3$ | CH$_2$cPr |
| I-B-82 | H | Cl | CH | CF$_3$ | CH$_2$SCH$_3$ |
| I-B-83 | H | Cl | CH | CF$_3$ | CH$_2$SOCH$_3$ |
| I-B-84 | H | Cl | CH | CF$_3$ | CH$_2$SO$_2$CH$_3$ |
| I-B-85 | H | Cl | CCl | CF$_3$ | CH$_3$ |
| I-B-86 | H | Cl | CCl | CF$_3$ | CH$_2$CH$_3$ |
| I-B-87 | H | Cl | CCl | CF$_3$ | CH$_2$CF$_3$ |
| I-B-88 | H | Cl | CCl | CF$_3$ | CH$_2$CH$_2$CH$_3$ |
| I-B-89 | H | Cl | CCl | CF$_3$ | iPr |
| I-B-90 | H | Cl | CCl | CF$_3$ | iBu |
| I-B-91 | H | Cl | CCl | CF$_3$ | cPr |
| I-B-92 | H | Cl | CCl | CF$_3$ | cBu |
| I-B-93 | H | Cl | CCl | CF$_3$ | CH$_2$cPr |
| I-B-94 | H | Cl | CCl | CF$_3$ | CH$_2$SCH$_3$ |
| I-B-95 | H | Cl | CCl | CF$_3$ | CH$_2$SOCH$_3$ |
| I-B-96 | H | Cl | CCl | CF$_3$ | CH$_2$SO$_2$CH$_3$ |
| I-B-97 | F | Cl | CCl | Cl | CH$_3$ |
| I-B-98 | F | Cl | CCl | Cl | CH$_2$CH$_3$ |
| I-B-99 | F | Cl | CCl | Cl | CH$_2$CF$_3$ |
| I-B-100 | F | Cl | CCl | Cl | CH$_2$CH$_2$CH$_3$ |
| I-B-101 | F | Cl | CCl | Cl | iPr |
| I-B-102 | F | Cl | CCl | Cl | iBu |
| I-B-103 | F | Cl | CCl | Cl | cPr |
| I-B-104 | F | Cl | CCl | Cl | cBu |
| I-B-105 | F | Cl | CCl | Cl | CH$_2$cPr |
| I-B-106 | F | Cl | CCl | Cl | CH$_2$SCH$_3$ |
| I-B-107 | F | Cl | CCl | Cl | CH$_2$SOCH$_3$ |
| I-B-108 | F | Cl | CCl | Cl | CH$_2$SO$_2$CH$_3$ |
| I-B-109 | H | CF$_3$ | CF | H | CH$_3$ |
| I-B-110 | H | CF$_3$ | CF | H | CH$_2$CH$_3$ |
| I-B-111 | H | CF$_3$ | CF | H | CH$_2$CF$_3$ |
| I-B-112 | H | CF$_3$ | CF | H | CH$_2$CH$_2$CH$_3$ |
| I-B-113 | H | CF$_3$ | CF | H | iPr |
| I-B-114 | H | CF$_3$ | CF | H | iBu |
| I-B-115 | H | CF$_3$ | CF | H | cPr |
| I-B-116 | H | CF$_3$ | CF | H | cBu |
| I-B-117 | H | CF$_3$ | CF | H | CH$_2$cPr |
| I-B-118 | H | CF$_3$ | CF | H | CH$_2$SCH$_3$ |
| I-B-119 | H | CF$_3$ | CF | H | CH$_2$SOCH$_3$ |
| I-B-120 | H | CF$_3$ | CF | H | CH$_2$SO$_2$CH$_3$ |
| I-B-121 | H | Cl | CCl | H | CH$_3$ |
| I-B-122 | H | Cl | CCl | H | CH$_2$CH$_3$ |
| I-B-123 | H | Cl | CCl | H | CH$_2$CF$_3$ |
| I-B-124 | H | Cl | CCl | H | CH$_2$CH$_2$CH$_3$ |
| I-B-125 | H | Cl | CCl | H | iPr |
| I-B-126 | H | Cl | CCl | H | iBu |
| I-B-127 | H | Cl | CCl | H | cPr |
| I-B-128 | H | Cl | CCl | H | cBu |
| I-B-129 | H | Cl | CCl | H | CH$_2$cPr |
| I-B-130 | H | Cl | CCl | H | CH$_2$SCH$_3$ |
| I-B-131 | H | Cl | CCl | H | CH$_2$SOCH$_3$ |
| I-B-132 | H | Cl | CCl | H | CH$_2$SO$_2$CH$_3$ |
| I-B-133 | H | Cl | CH | H | CH$_3$ |
| I-B-134 | H | Cl | CH | H | CH$_2$CH$_3$ |
| I-B-135 | H | Cl | CH | H | CH$_2$CF$_3$ |
| I-B-136 | H | Cl | CH | H | CH$_2$CH$_2$CH$_3$ |
| I-B-137 | H | Cl | CH | H | iPr |
| I-B-138 | H | Cl | CH | H | iBu |
| I-B-139 | H | Cl | CH | H | cPr |
| I-B-140 | H | Cl | CH | H | cBu |
| I-B-141 | H | Cl | CH | H | CH$_2$cPr |
| I-B-142 | H | Cl | CH | H | CH$_2$SCH$_3$ |
| I-B-143 | H | Cl | CH | H | CH$_2$SOCH$_3$ |
| I-B-144 | H | Cl | CH | H | CH$_2$SO$_2$CH$_3$ |

$^1$H-NMR Data $^1$H-NMR-data were determined with a Bruker Avance 400 equipped with a flow cell (60 µl volume) or with a Bruker AVIII 400 equipped with 1.7 mm cryo-CPTCI probe head or with a Bruker AVII 600 (600.13 MHz) equipped with a cyroTCI probe head or with a Bruker AVIII 600 (601.6 MHz) equipped with a cryo CPMNP probe head with tetramethylsilane as reference (0.0) and the solvents CD$_3$CN, CDCl$_3$, [D$_6$]-DMSO.

NMR-data of selected examples are listed in classic format (chemical shift δ, multiplicity, number of hydrogen atoms) or as NMR-peak-lists.

NMR-Peak-Lists:

If NMR-data of selected examples are provided in form of $^1$H-NMR-peak lists, then for every peak first the chemical shift δ in ppm and then, separated by a blank, the intensity of the signal in round brackets is listed.

The peak list of an example is therefore listed as: δ$_1$ (intensity$_1$); δ$_2$ (intensity$_2$); . . . ; δ$_i$ (intensity$_i$); . . . ; δ$_n$ (intensity$_n$).

The solvent, in which the NMR-spectrum was measured, is specified in squared brackets.

TABLE 3

| Ex. No. | NMR |
|---|---|
| I-A-38 | $^1$H-NMR (400 MHz, CD$_3$CN): δ = 1.07-1.11 (t, 3H), 1.73-1.82 (m, 2H), 2.11-2.14 (m, 2H), 2.39-2.48 (m, 1H), 2.74-2.85 (m, 1H), 2.89-3.03 (m, 1H), 3.54-3.63 (m, 1H), 3.84-3.86 ("d", 1H), 5.24-5.30 (q, 1H), 6.01-6.04 (m, 1H), 6.48-6.50 (d, br, 1H), 6.67-6.72 (m, 1H), 6.74-6.75 ("d", 1H), 8.04 (s, 1H), 8.05 (s, 2H). |
| I-A-43 | 1H-NMR (400 MHz, CD$_3$CN): δ = 0.69-0.73 (m, 2H), 0.75-0.84 (m, 2H), 1.43-1.49 (m, 1H), 1.76-1.84 (m, 2H), 2.11-2.18 (m, 2H), 2.41-2.48 (m, 1H), 2.77-2.85 (m, 1H), 2.93- |

TABLE 3-continued

| Ex. No. | NMR |
|---|---|
| | 3.03 (m, 1H), 3.54-3.62 (m, 1H), 3.81-3.83 (d, 1H), 5.25-5.30 (q, 1H), 6.02-6.05 (m, 1H), 6.68-6.80 (m, 3H), 7.13-7.15 (d, 1H), 8.04 (s, 1H), 8.06 (s, 2H). |
| I-A-9 | $^1$H-NMR (400 MHz, CD$_3$CN): δ = 0.13-0.18 (m, 2H), 0.48-0.52 (m, 2H), 0.84-0.90 (m, 1H), 1.77-1.80 (m, 1H), 2.04-2.06 (d, 2H), 2.41-2.49 (m, 1H), 2.71-2.79 (m, 1H), 2.81-2.88 (m, 2H), 3.46-3.59 (m, 2H), 3.76 (br, 1H), 5.26-5.32 (q, 1H), 5.89-5.92 (m 1H), 6.52-6.54 (d, br, 1H), 6.66-6.70 (m 1H), 6.72 (m, 1H), 7.12-7.14 (d, 1H), 7.47 (m, 2H), 7.49-7.50 (d, 1H). |
| I-A-45 | $^1$H-NMR (400 MHz, d$_6$-DMSO): δ = 0.11-0.15 (m, 2H), 0.40-0.46 (m, 2H), 0.98-1.06 (m, 1H), 1.69-1.78 (m, 1H), 2.00-2.02 (d, 2H), 2.30-2.40 (m, 1H), 2.72-2.81 (m, 2H), 2.87-2.94 (m, 1H), 3.05-3.08 (m, 1H), 3.44-3.50 (m, 2H), 5.16-5.22 (q, 1H), 5.88-5.90 (d, br, 1H), 6.02-6.04 (d, 1H), 6.63-6.66 (d, 1H), 6.79 (s, 1H), 7.04-7.06 (d, 1H), 8.14 (s, 2H), 8.16 (s, 1H). |
| I-A-19 | $^1$H-NMR (400 MHz, CD$_3$CN): δ = 0.66-0.70, (m, 2H), 0.76-0.81 (m, 2H), 1.43-1.48 (m, 1H), 1.76-1.81 (m, 1H), 2.39-2.47 (m, 1H), 2.67-2.98 (3m, 4H), 3.46-3.59 (2H), 3.95-3.97 (d, 1H), 5.23-5.29 (q, 1H), 5.88-5.91 (m, 1H), 6.65-6.69 (m, 1H), 6.71-6.72 (d, 1H), 6.83-8.85 (s, br, 1H), 7.11-7.13 (d, 1H), 7.63 (s, 2H). |
| I-A-127 | $^1$H-NMR (400 MHz, CD$_3$CN): δ = 0.66-0.70, (m, 2H), 0.76-0.81 (m, 2H), 1.43-1.48 (m, 1H), 1.74-1.83 (m, 1H), 2.39-2.47 (m, 1H), 2.68-2.99 (3m, 4H), 3.49-3.57 (m, 2H), 3.68 (br, 1H), 5.24-5.29 (q, 1H), 5.90-5.91 (d, 1H), 6.66-6.70 (m, 1H), 6.73 (m, 1H), 6.76-6.78 (d, br, 1H), 7.12-7.14 (d, 1H), 7.39-7.66 (m, 3H). |
| I-A-21 | $^1$H-NMR (400 MHz, CD$_3$CN): δ = 0.13-0.18 (m, 2H), 0.48-0.52 (m, 2H), 0.96-1.06 (m, 1H), 1.73-1.83 (m, 1H), 2.04-2.06 (d, 2H), 2.41-2.49 (m, 1H), 2.67-2.98 (m, 4H), 3.46-3.59 (m, 2H), 3.75-3.77 (d, 1H), 5.27-5.32 (q, 1H), 5.88-5.91 (m, 1H), 6.51-6.53 (d, br, 1H), 6.57-6.69 (m, 1H), 6.72 (m, 1H), 7.12-7.14 (d, 1H), 7.63 (s, 2H). |
| I-A-33 | $^1$H-NMR (400 MHz, d$_6$-DMSO): δ = 0.13-0.14 (m, 2H), 0.42-0.46 (m, 2H), 0.98-1, 02 (m, 1H), 1.71-1.76 (m, 1H), 2.01 (d, 2H), 2.33-2.36 (m, 1H), 2.72-2.96 (m, 4H), 3.41-3.43 (m, 2H), 5.19 (m, 1H), 5.81 (m, 1H), 6.01-6.94 (m, 1H), 6.65-6.72 (m, 2H), 7.04-7.06 (m, 1H), 7.84 (m, 1H), 7.93-7.95 (m, 1H). |
| I-A-26 | $^1$H-NMR (400 MHz, d$_6$-DMSO): δ = 1.05 (t, 3H), 1.68-1.77 (m, 1H), 2.06-2.13 (m, 2H), 2.30-2.38 (m, 1H), 2.67-2.79 (m, 2H), 2.86-3.00 (m, 2H), 3.32-3.43 (m, 2H), 5.17 (m, 1H), 5.78-5.83 (m, 1H), 6.01-6.04 (m, 1H), 6.59-6.73 (m, 2H), 7.84 (m, 1H), 7.98-8.00 (m, 1H). |
| I-A-31 | $^1$H-NMR (400 MHz, d$_6$-DMSO): δ = 0.68-0.88 (m, 4H), 1.54-1.61 (m, 1H), 1.70-1.79 (m, 1H), 2.30-2.40 (m, 1H), 2.67-2.78 (m, 2H), 2.87-3.07 (m, 2H), 3.42-3.43 (m, 2H), 5.17 (m, 1H), 5.79-5.83 (m, 1H), 6.03-6.05 (m, 1H), 6.44-6.73 (m, 2H), 7.05-7.07 (m, 1H), 7.85 (m, 1H), 8.29-8.39 (m, 1H). |
| I-A-115 | $^1$H-NMR (400 MHz, CD$_3$CN): d = 0.65-0.84 (m, 4H), 1.42-1.49 (m, 1H), 1.75-1.84 (m, 1H), 2.39-2.48 (m, 1H), 2.70-2.95 (m, 4H), 3.49-3.62 (m, 2H), 3.72-3.73 (m, 1H), 5.24-5.30 (m, 1H), 5.92-5.95 (m, 1H), 6.69-6.80 (m, 3H), 7.12-7.15 (d, 1H), 7.38-7.42 (m, 1H), 7.76-7.79 (m, 2H). |
| I-A-139 | $^1$H-NMR (400 MHz, CD$_3$CN): δ = 0.67-0.69 (m, 2H), 0.77-0.81 (m, 2H), 1.43- 1.47 (m, 1H), 1.72-1.82 (m, 1H), 2.38-2.47 (m, 1H), 2.50-2.53 (m, 1H), 2.57-2.67 (m, 1H), 2.73-2.81 (m, 1H), 2.84-2.96 (m, 2H), 3.36-3.41 (m 1H), 3.45-3.56 (m, 1H), 3.79-3.82 (d, 1H), 4.07-4.09 (d, 1H), 5.21-5.27 (q, 1H), 6.48-6.51 (d, 1H), 6.53 (s, 1H), 6.70-6.73 (d, br, 1H), 7.08-7.10 (d 1H), 7.41-7.47 (m, 2H), 7.51-7.54 (m, 2H). |
| I-A-7 | $^1$H-NMR (400 MHz, CD$_3$CN): δ = 0.66-0.73 (m, 2H), 0.74-0.84 (m, 2H), 1.40-1.48 (m, 1H), 1.75-1.84 (m, 1H), 2.38-2.47 (m, 1H), 2.68-2.99 (3m, 4H), 3.47-3.60 (2H), 3.72-3.73 (d, 1H), 5.24-5.30 (q, 1H), 5.91 (s, br, 1H), 6.66-6.77 (m, 3H), 7.12-7.14 (d, 1H), 7.46-7.50 (m, 3H) ppm |
| I-A-13 | $^1$H-NMR (400 MHz, CD$_3$CN): δ 1.72-1.81 (m, 1H), 1.85, 1.88 (2s, 3H), 2.37-2.47 (m, 1H), 2.69-2.97 (3m, 4H), 3.46-3.59 (m, 2H), 3.72-3.74 (d, 1H), 5.22-5.27 (q, 1H), 5.88-5.91 (m, 1H), 6.48-6.60 (m, 2H), 6.65-6.71 (m, 2H), 7.12-7.14 (d, 1H), 7.63 (s, 2H) ppm |
| I-A-37 | $^1$H-NMR (400 MHz, CD$_3$CN): δ = 1.72-1.82 (m, 1H), 1.84, 1.87 (2s, 3H), 2.37-2.48 (m, 1H), 2.76-2.84 (m, 2H), 2.91-3.03 (m, 2H), 3.54-3.64 (m, 2H), 3.86-3.88 (d, br, 1H), 5.22-5.28 (q, 1H), 6.02-6.04 (m, 1H), 6.51-6.57 (m, br, 1H), 6.68-6.75 (m, 2H), 7.13-7.15 (d, 1H), 8.04 (s, 1H), 8.06 (s, 2H) ppm |
| I-A-40 | $^1$H-NMR (400 MHz, CD$_3$CN): δ = 0.91-0.95 (t, 3H), 1.55-1.68 (m, 2H), 1.73-1.82 (m, 1H), 2.10-2.12 (tr, 2H), 2.40-2.48 (m, 1H), 2.76-2.84 (m, 2H), 2.89-3.03 (m, 2H), 3.54-3.64 (m, 2H), 3.78-3.79 (m, br, 1H), 5.25-5.31 (q, 1H), 6.01-6.04 (m, 1H), 6.50-6.54 (m, br, 1H), 6.68-6.75 (m, 2H), 7.12-7.14 (d, 1H), 8.04 (s, 1H), 8.05 (s, 2H) ppm |
| I-A-18 | $^1$H-NMR (400 MHz, CD$_3$CN): δ 0.93-0.95 (2d, 6H) 1.72-1.81 (m, 1H), 1.96-2.14 (m, 3H), 2.39-2.47 (m, 1H), 2.69-2.97 (3m, 4H), 3.46-3.59 (m, 2H), 3.70-3.72 (d, 1H), 5.25-5.31 (q, 1H), 5.88-5.91 (m, 1H), 6.45-6.72 (s + m, 2H), 7.11-7.13 (d, 1H), 7.63 (s, 2H) ppm |
| I-A-1 | $^1$H-NMR (400 MHz, CD$_3$CN): δ = 1.72-1.81 (m, 1H), 1.84, 1.88 (2s, 3H), 2.33-2.46 (m, 1H), 2.68 -2.97 (m, 4H), 3.46-3.59 (m, 2H), 3.75-3.77 (d, br, 1H), 5.21-5.27 (q, 1H), 5.87-5.92 (m 1H), 6.50-6.59, 6.65-6.70 (m, br, 3H), 6.72 ("d", 1H), 7.12-7.14 (d, 1H), 7.47 (s, 2H), 7.49 (d, 1H) ppm |
| I-A-79 | $^1$H-NMR (400 MHz, CD$_3$CN): δ = 0.65-0.74 (m, 2H), 0.76-0.84 (m, 2H), 1.39-1.49 (m, 1H), 1.74-1.84 (m, 1H), 2.10-2.13 (m, 1H) 2.39-2.48 (m, 1H), 2.69-2.99 (2m, 4H), 3.49-3.62 (m, 2H), 3.91-3.93 (d, 1H), 5.24-5.30 (q, 1H), 5.96-5.98 (d, br, 1H), 6.52-6.74 (m, 2H), 6.80-6.82 (d, br 1H) 7.13-7.15 (d, 1H), 7.73 (s, 1H), 7.61 (s, 1H), 7.79 (s, 1H) ppm |
| I-A-6 | $^1$H-NMR (400 MHz, CD$_3$CN): δ = 0.93-0.95 (2d, 6H), 1.72-1.81 (m, 1H), 1.97-2.12 (m, 3H), 2.34-2.47 (m, 1H), 2.69 -2.97 (m, 4H), 3.46-3.59 (m, 2H), 3.81-3.83 (d, 1H), 5.25-5.31 (q, 1H), 5.89-5.91 (m, 1H), 6.50-6.59, 6.65-6.69 (m, 2H), 6.71-6.72 (d, br, 1H), 7.11-7.13 (d, 1H), 7.47 (s, 2H), 7.49-7.50 (d, 1H) ppm |
| I-A-42 | $^1$H-NMR (400 MHz, CD$_3$CN): δ = 0.93-0.95 (2 d, 6H), 1.73-1.82 (m, 1H), 1.96-2.12 (m, 3H), 2.33-2.48 (m, 1H), 2.77-2.84 (m, 2H), 2.91-3.03 (m, 2H), 3.51-3.63 (m, 2H), 3.90 |

TABLE 3-continued

| Ex. No. | NMR |
|---|---|
| | (s, br, 1H), 5.26-5.32 (q, 1H), 6.02-6.03 (d, br, 1H), 6.51-6.59 (m, 1H), 6.66-6.72 (m, 1H), 6.74-6.75 (d, br, 1H), 7.12-7.14 (d, 1H), 8.04 (s, 1H), 8.05 (s, 2H) ppm |
| I-A-16 | $^1$H-NMR (400 MHz, CD$_3$CN): δ 0.92 (t, 3H), 1.58-1.64 (m, 2H), 1.72-1.81 (m, 1H), 2.05-2.12 (m, 2H), 2.39-2.47 (m, 1H), 2.67-2.97 (m, 4H), 3.46-3.59 (m, 2H), 3.83 (s, br, 1H), 5.25-5.30 (q, 1H), 5.87-5.90 (m, 1H), 6.47-6.59 (m, 1H), 6.64-6.69 (m, 1H), 6.71-6.75 (d, br, 1H), 7.11-7.13 (d, 1H), 7.63 (s, 2H) ppm |
| I-A-14 | $^1$H-NMR (400 MHz, CD$_3$CN): δ 1.06, 1.09 (2t, 3H), 1.58-1.64 (m, 2H), 1.72-1.81 (m, 1H), 2.11-2.14 (m, 2H), 2.39-2.47 (m, 1H), 2.67-2.97 (m, 4H), 3.46-3.59 (m, 2H), 3.77-3.78 (d, br, 1H), 5.24-5.30 (q, 1H), 5.88-5.91 (m, 1H), 6.43-6.60 (m, 1H), 6.65-6.69 (m, 1H), 6.71 (d, br, 1H), 7.11-7.13 (d, 1H), 7.63 (s, 2H) ppm |
| I-A-4 | $^1$H-NMR (400 MHz, CD$_3$CN): δ = 0.93 (t, 3H), 1.54-1.64 (m, 2H), (1.72-1.81 (m, 1H), 2.05-2.12 (m, 2H), 2.34-2.47 (m, 1H), 2.68-2.97 (m, 4H), 3.46-3.59 (m, 2H), 3.74-3.76 (d, 1H), 5.25-5.30 (q, 1H), 5.89-5.92 (m, 1H), 6.45-6.59 (m, 1H), 6.65-6.69 (m, 1H), 6.71-6.72 (d, br, 1H), 7.11-7.13 (d, 1H), 7.47 (s, 2H), 7.49-7.50 (d, 1H) ppm |
| I-B-2 | $^1$H-NMR (300 MHz, CDCl$_3$): δ = 1.20 (t, 3H), 1.83 (m, 1H), 2.26 (q, 2H), 2.61-2.75 (m, 2H), 2.85-3.30 (m, 3H), 3.75 (m, 1H), 3.87 (m, 1H), 5.46-5.56 (m, 2H), 7.23-7.62 (m, 4H). |
| I-B-115 | $^1$H-NMR (300 MHz, CDCl$_3$): δ = 0.65-0.73 (m, 2H), 0.78-0.84 (m, 2H), 1.44-1.51 (m, 1H), 1.77-1.80 (m, 1H), 2.42-2.53 (m, 1H), 2.80-3.02 (m, 4H), 3.67-3.73 (m, 1H), 3.85-3.92 (m, 1H), 5.31-5.40 (m, 1H), 6.85-6.92 (m, 1H), 7.28-7.29 (d, 1H), 7.38-7.51 (m, 3H), 8.01-8.10 (m, 2H). |

Synthesis of Intermediates (II)

The synthesis of intermediates of formula (II) is described in WO 2010/043315 and is exemplified by the following example:

Synthesis of N-(5-{3-[3,5-bis(trifluoromethyl)phenyl]-3-(trifluoromethyl)pyrrolidin-1-yl}-2,3-dihydro-1H-inden-1-yl)propanamide

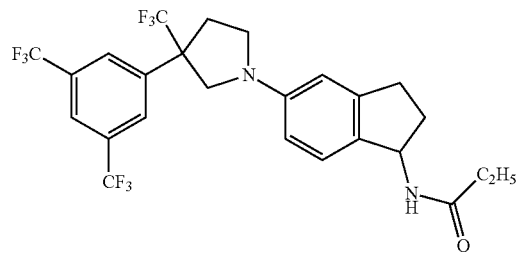 [SMILES: CCC(=O)NC1CCc2cc(N3CCC(c4cc(C(F)(F)F)cc(C(F)(F)F)c4)(C(F)(F)F)C3)ccc21]

Step 1

Synthesis of 5-bromo-N-hydroxyindan-1-imine

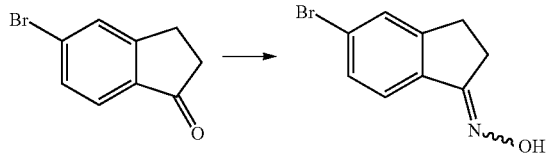 [SMILES: O=C1CCc2cc(Br)ccc21 ; ON=C1CCc2cc(Br)ccc21]

5-Bromoindan-1-one (5.0 g) was dissolved in methanol. Hydroxylammonium chloride (2.5 g) and sodium acetate (2.9 g) were added to the solution at room temperature, and then stirred overnight.

The reaction solution was diluted with water and extracted twice with ethyl acetate. The organic layers were combined, washed with water, and dried over anhydrous magnesium sulfate. The desiccant was filtered and separated, and then the solvent was evaporated off under reduced pressure to obtain 5-bromo-N-hydroxyindan-1-imine (5.1 g).

$^1$H-NMR (DMSO-d$_6$) δ: 2.76-2.81 (2H, m), 2.98-3.03 (2H, m), 7.41-7.49 (2H, m), 7.59 (1H, s), 10.98 (1H, s).

Step 2

Synthesis of N-(5-bromo-2,3-dihydro-1H-inden-1-yl)propanamide

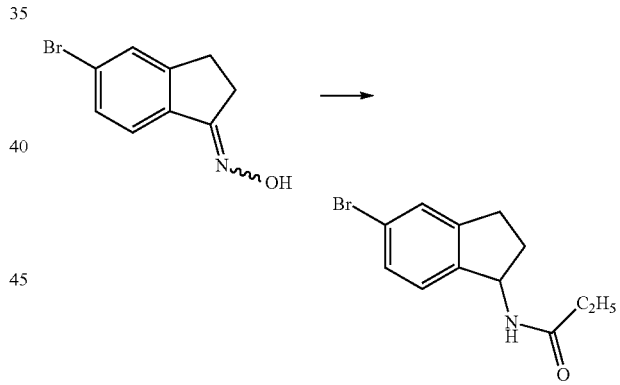

5-Bromo-N-hydroxyindan-1-imine (2.0 g), propionic acid anhydride (2.3 g) and nickel chloride dihydrate (1.1 g) were dissolved in methanol. Sodium borohydride (1.3 g) was slowly added to the solution under ice cooling, and the mixture was stirred for 30 minutes. Diethylenetriamine (2.9 ml) was added to the reaction solution, which was heated back to room temperature, and stirred for 30 minutes. The mixture was diluted with ethyl acetate and water, and stirred for 5 minutes. The organic layer was separated and the aqueous layer was extracted with ethyl acetate. The organic layers were combined, washed with saturated sodium bicarbonate aqueous solution, and dried over magnesium sulfate. The desiccant was filtered and separated, and the solvent was evaporated off under reduced pressure. The residue was separated and purified by a column chromatography to obtain N-(5-bromo-2,3-dihydro-1H-inden-1-yl) propanamide (1.1 g).

¹H NMR (acetone-d₆) δ: 1.19 (3H, t), 1.84-1.96 (1H, m), 2.26 (2H, q), 2.49-2.60 (1H, m), 2.88-3.10 (2H, m), 5.36-5.46 (1H, m), 6.65 (1H, s), 7.24 (1H, d), 7.44 (1H, d), 7.51 (1H, s).

Step 3

Synthesis of N-(5-{3-[3,5-bis(trifluoromethyl)phenyl]-3-(trifluoro-methyl)pyrrolidin-1-yl}-2,3-dihydro-1H-inden-1-yl)propanamide

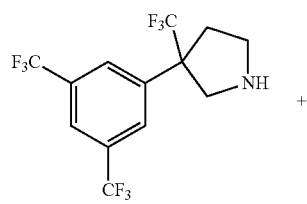

3-[3,5-bis(trifluoromethyl)phenyl]-3-(trifluoromethyl) pyrrolidine (0.46 g) and N-(5-bromo-2,3-dihydro-1H-inden-1-yl)propanamide (0.35 g) were dissolved in toluene and deaeration procedure was performed three times under argon atmosphere. Sodium tert-butoxide (0.25 g), Xantphos (0.05 g) and tris(dibenzylideneacetone)dipalladium (0) (chloroform adduct) (0.03 g) were added to the mixture and heated and stirred at 100° C. under argon atmosphere for 2 hours. The solution was cooled to room temperature and the reaction liquid was diluted with ethyl acetate followed by washing with water and brine. The organic layer was dried over anhydrous magnesium sulfate. The desiccant was filtered and separated, the solvent was evaporated off under reduced pressure, and the residue was purified by a silica gel chromatography to obtain N-(5-{3-[3,5-bis(trifluoromethyl)phenyl]-3-(trifluoro-methyl)pyrrolidin-1-yl}-2,3-dihydro-1H- -inden-1-yl)propanamide (0.51 g).

¹H-NMR (CDCl₃) δ: 1.18 (3H, t), 1.75-1.86 (1H, m), 2.23 (2H, q), 2.54-2.64 (2H, m), 2.79-3.02 (3H, m), 3.47-3.64 (2H, m), 3.84 (1H, d), 4.15 (1H, d), 5.38-5.57 (2H, m), 6.52-6.49 (2H, m), 7.20 (1H, d), 7.85 (2H, s), 7.91 (1H, s).

Pyrrolidin Intermediates of the Formula (Int-1)

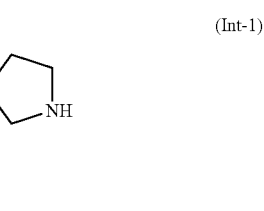

are known and described in JP 2008/110971, WO 2008(128711, WO 2010/043315, WO 2011/080211 and JP 2011/136928.

Further synthetic examples of intermediates (Int-1):

Synthesis of 3-(3,5-dichloro-4-fluorophenyl)-3-(trifluoromethyl)pyrrolidine (Int-1-1)

Step 1

Synthesis of 1,5-dichloro-2-fluoro-3-(3,3,3-trifluoroprop-1-en-2-yl)benzene

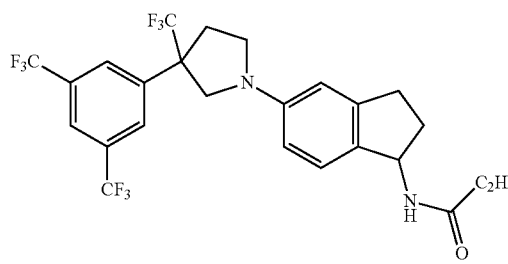

1-Bromo-3,5-dichloro-2-fluorobenzene (10 g), (3,3,3-trifluoroprop-1-en-2-yl)-boronic acid (7.5 g:) and potassium carbonate (13.6 g) were dissolved in tetrahydrofuran (41 ml) and water (20 ml), and then deaerated. Dichlorobis(triphenylphosphine)palladium (II) (1.4 g) was added thereto and the mixture was stirred for 3 hours under reflux under argon atmosphere. After cooling the mixture to the room temperature, water and n-hexane were added, and the organic layer was washed with water and dried over anhydrous magnesium sulfate. The drying agent was filtered off, the solvent was distilled off under reduced pressure, and the residue was roughly purified by silica gel chromatography (n-hexane) to obtain a mixture containing 1,3-dichloro-2,4-difluoro-5-(3,3, 3-trifluoroprop-1-en-2-yl)benzene and hexane.

¹H-NMR (CDCl₃) δ: 5.82 (1H, s), 6.25 (1H, s), 7.21-7.26 (1H, m), 7.48-7.43 (1H, m).

Step 2

Synthesis of 1-benzyl-3-(3,5-dichloro-2-fluorophenyl)-3-(trifluoromethyl)pyrrolidine

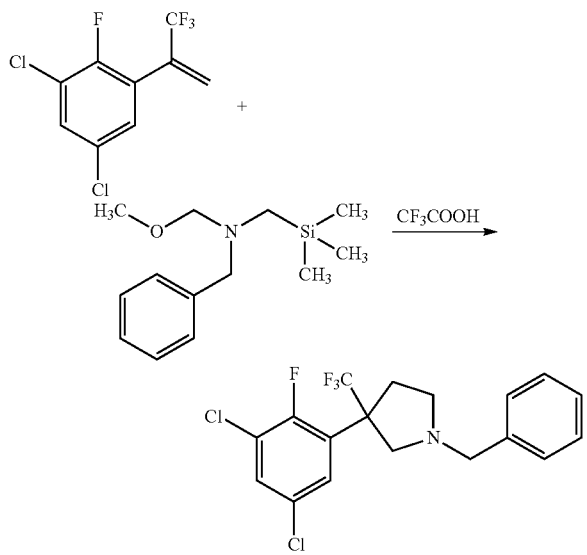

1,5-Dichloro-2-fluoro-3-(3,3,3-trifluoroprop-1-en-2-yl)benzene (6.2 g) and N-(methoxymethyl)-N-(trimethylsilylmethyl)benzylamine (4.7 g) were dissolved in dichloromethane (100 ml) and slowly added dropwise with a dichloromethane solution (8 ml) of anhydrous trifluoroacetic acid (0.15 ml) under ice cooling. Upon the completion of the dropwise addition, the reaction temperature was raised to room temperature and stirred overnight. The reaction solution was concentrated under reduced pressure, and the residue was purified by column chromatography to obtain 1-benzyl-3-(3,5-dichloro-2-fluorophenyl)-3-(trifluoromethyl)pyrrolidine (3.7 g).

¹H NMR (CDCl₃) δ: 2.38-2.45 (1H, m), 2.56-2.70 (2H, m), 2.84-2.89 (1H, m), 3.02 (1H, d), 3.40 (1H, dd), 3.65 (1H, d), 3.70 (1H, d), 7.17 (1H, dd), 7.26-7.34 (5H, m), 7.40 (1H, dd).

Step 3

Synthesis of 3-(3,5-dichloro-4-fluorophenyl)-3-(trifluoromethyl)pyrrolidine (Int-1-1)

(Int-1-1)

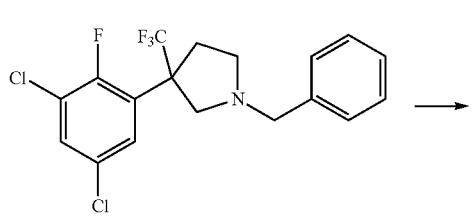

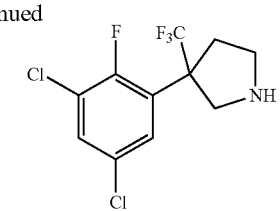

1-Benzyl-3-(3,5-dichloro-4-fluorophenyl)-3-(trifluoromethyl)pyrrolidine (3.7 g) was dissolved in 1,2-dichloroethane (20 ml), added with 1-chloroethyl chloroformate (2.7 g) at room temperature, and then refluxed under heating for 3 hours. The reaction solution was concentrated under reduced pressure, and the residue obtained was added with methanol (30 ml) and further refluxed under heating for 2 hours. The reaction solution was concentrated under reduced pressure and the residue obtained was added with t-butyl methyl ether and water to separate the aqueous layer. After that, the organic layer was again washed with a 1 M aqueous solution of hydrochloric acid, and the aqueous layers were combined, added with a saturated aqueous solution of potassium carbonate to make the liquid alkaline, and extracted with t-butyl methyl ether. The aqueous phase was extracted again with t-butyl methyl ether, and the organic layers were combined, dried over magnesium sulfate, filtered and concentrated under reduced pressure to obtain 3-(3,5-dichloro-4-fluorophenyl)-3-(trifluoromethyl)pyrrolidine (2.6 g).

¹H NMR (CDCl₃) δ: 2.27-2.34 (1H, m), 2.61-2.68 (1H, m), 2.99-3.05 (1H, m), 3.29-3.17 (2H, m), 3.94 (1H, dd), 7.20 (1H, dd), 7.42 (1H, dd).

Synthesis of 2,6-bis(trifluoromethyl)-4-[3-(trifluoromethyl)pyrrolidin-3-yl]pyridine (Int-1-2)

Step 1

Synthesis of 4-[1-benzyl-3-(trifluoromethyl)pyrrolidin-3-yl]-2,6-bis(trifluoromethyl)pyridine To the solution of 2,6-bis(trifluoromethyl)-4-(3,3,3-trifluoroprop-1-en-2-yl)pyridine (1.25 g) and N-benzyl-1-methoxy-N-[(trimethylsilyl)methyl]methanamine (5.0 g) in dichloromethane was added dropwise the solution of trifluoroacetic acid (0.038 g) in dichloromethane while cooling with ice. On completion of the dropwise addition, the mixture was warmed to room temperature and stirred over night. The mixture was washed with saturated sodium bicarbonate water and dried over anhydrous magnesium sulfate. After the drying agent was filtered off, the solvent was removed under reduced pressure, and the residue was then purified by silica gel chromatography to yield 4-[1-benzyl-3-(trifluoromethyl)pyrrolidin-3-yl]-2,6-bis(trifluoromethyl)pyridine (1.52 g).

$^1$H-NMR (CDCl$_3$) δ: 2.23-2.29 (1H, m), 2.65-2.69 (2H, m), 2.96 (1H, d), 3.05-3.15 (2H, m), 3.58 (1H, d), 3.82 (1H, d), 7.26-7.37 (5H, m), 8.00 (2H, s).

Step 2

Synthesis of 2,6-bis(trifluoromethyl)-4-[3-(trifluoromethyl)pyrrolidin-3-yl]pyridine (Int-1-2)

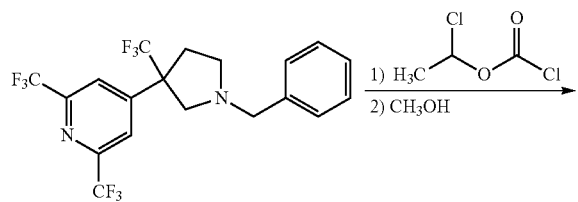

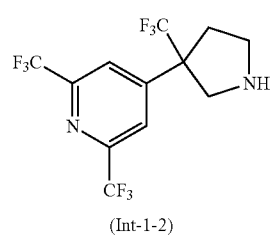

(Int-1-2)

The solution of 4-[1-benzyl-3-(trifluoromethyl)pyrrolidin-3-yl]-2,6-bis(trifluoromethyl)pyridine (1.4 g) and 1-chloroethyl chloroformate (0.905 g) in dichloroethane was heated to reflux for 3 hours. The mixture was cooled to room temperature and then concentrated under the reduced pressure. Methanol was added to the resultant residue, which was then heated with stirring at 60° C. for two hours. The mixture was cooled to room temperature, to which was then added water. The solution was washed twice with the mixed solvent of hexane. The solution was neutralized with sodium hydroxide and then extracted with tert-butyl methyl ether three times. The organic layers were combined, washed with brine and dried over anhydrous magnesium sulfate. After the drying agent was filtered off, the solvent was removed under reduced pressure to yield 2,6-bis(trifluoromethyl)-4-[3-(trifluoromethyl)pyrrolidin-3-yl]pyridine (0.781 g).

$^1$H NMR (CDCl$_3$) δ: 1.86 (1H, br s), 2.27-2.36 (1H, m), 2.63-2.69 (1H, m), 3.05-3.14 (1H, m), 3.26-3.33 (2H, m), 3.83 (1H, d), 7.87 (2H, s).

Synthesis of 3-(3,5-dichloro-2,4-difluorophenyl)-3-(trifluoromethyl)pyrrolidine (Int-1-3)

Step 1

Synthesis of 1,3-dichloro-2,4-difluoro-5-iodobenzene

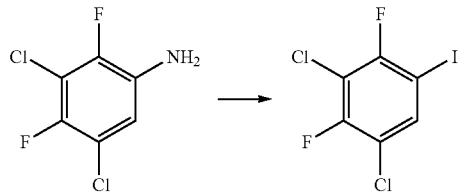 [SMILES: Nc1cc(Cl)c(F)c(Cl)c1F ; Fc1c(Cl)cc(I)c(F)c1Cl]

To a mixture of 3,5-dichloro-2,4-difluoroaniline (5.0 g), an aqueous 57% solution of hydroiodic acid (20 ml) and water (20 ml), copper iodide (1.92 g) was added. The reaction liquid was maintained at 30° C. or less in a water bath.

To the reaction mixture was added dropwise a water solution (2 mL) of sodium nitrite (1.74 g). The reaction mixture was stirred for 10 minutes, maintained at 30° C. or less in a water bath. To the reaction mixture was added dropwise an aqueous solution (2 mL) of sodium nitrite (1.74 g), again. The reaction mixture was further stirred for 10 minutes, maintained at 30° C. or less in a water bath. To the reaction mixture was added dropwise a aqueous solution (2 mL) of sodium nitrite (1.74 g), again. t-Butyl methyl ether was added and the mixture was washed with water and with an aqueous solution of sodium sulfite and brine, and dried over anhydrous magnesium sulfate. The drying agent was filtered off, the solvent was distilled off under reduced pressure and the residue was purified by silica gel chromatography (n-hexane) to obtain 1,3-dichloro-2,4-difluoro-5-iodobenzene (6.0 g).

$^1$H-NMR (CDCl$_3$) δ: 7.6-7.75 (1H, m).

Step 2

Synthesis of 1,3-dichloro-2,4-difluoro-5-(3,3,3-trifluoroprop-1-en-2-yl)benzene

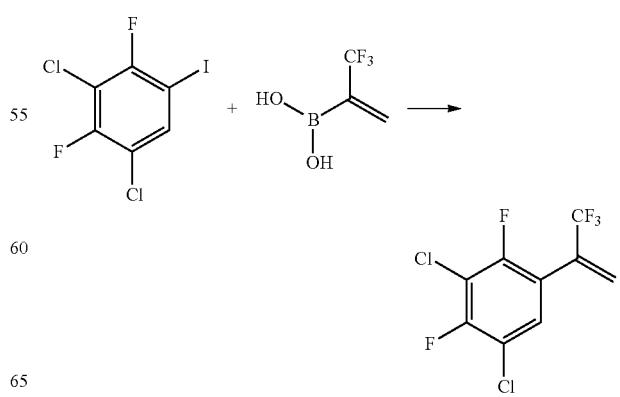

1,3-Dichloro-2,4-difluoro-5-iodobenzene (9.7 g), (3,3,3-trifluoroprop-1-en-2-yl)-boronic acid (10.5 g: 50% tetrahydrofuran solution) and potassium carbonate (10.4 g) were dissolved in tetrahydrofuran (44 ml) and water (22 ml), and then deaerated.

Dichlorobis(triphenylphosphine)palladium (II) (1.1 g) was added thereto and the mixture was stirred for 3 hours under reflux under argon atmosphere. After cooling the mixture to the room temperature, water and n-hexane were added, and the organic layer was washed with water and dried over anhydrous magnesium sulfate. The drying agent was filtered off, the solvent was distilled off under reduced pressure, and the residue was purified by silica gel chromatography (n-hexane) to obtain a mixture containing 1,3-dichloro-2,4-difluoro-5-(3,3,3-trifluoroprop-1-en-2-yl)benzene.

$^1$H-NMR (CDCl$_3$) δ: 5.81 (1H, s), 6.27 (1H, s), 7.3 (1H, t).

Step 3

Synthesis of 1-benzyl-3-(3,5-dichloro-2,4-difluorophenyl)-3-(trifluoromethyl)-pyrrolidine

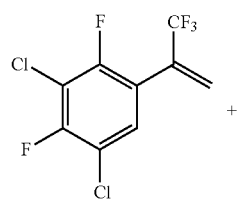

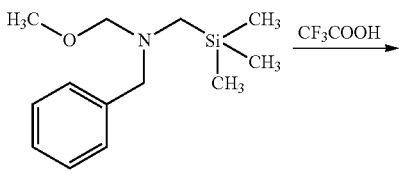

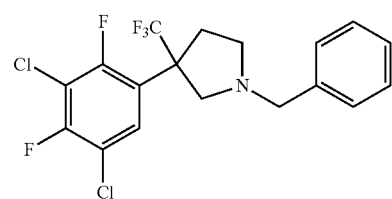

1,3-Dichloro-2,4-difluoro-5-(3,3,3-trifluoroprop-1-en-2-yl)benzene (2.8 g) and N-(methoxymethyl)-N-(trimethylsilylmethyl)benzylamine (2.0 g) were dissolved in dichloromethane (50 ml) and to the solution was slowly added dropwise a dichloromethane solution (0.8 ml) of anhydrous trifluoroacetic acid (0.065 ml) under ice cooling.

Upon the completion of the dropwise addition, the reaction temperature was raised to room temperature and stirred overnight. The reaction solution was concentrated under reduced pressure, and the residue was purified by silica gel column chromatography to obtain 1-benzyl-3-(3,5-dichloro-2,4-difluorophenyl)-3-(trifluoromethyl)pyrrolidine (1.9 g).

$^1$H-NMR (CDCl$_3$) δ: 2.34-2.43 (1H, m), 2.57-2.70 (2H, m), 2.79-2.90 (1H, m), 3.01 (1H, dd), 3.38 (1H, dd), 3.67 (2H, s), 7.22-7.33 (6H, m).

Step 4

Synthesis of 3-(3,5-dichloro-2,4-difluorophenyl)-3-(trifluoromethyl)pyrrolidine (Int-1-3)

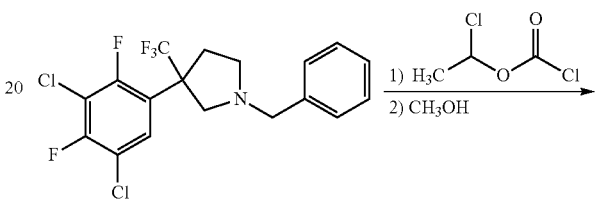

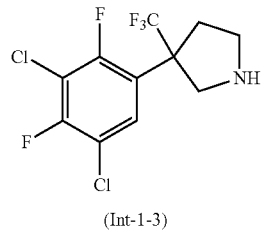

(Int-1-3)

1-Benzyl-3-(3,5-dichloro-2,4-difluorophenyl)-3-(trifluoromethyl)pyrrolidine (1.9 g) was dissolved in 1,2-dichloroethane (20 ml) and to the solution was added 1-chloroethyl chloroformate (1.3 g) at room temperature, and then refluxed under heating for 3 hours.

The reaction solution was concentrated under reduced pressure, and to the residue obtained was added methanol (30 ml) and further refluxed under heating for 2 hours. The reaction solution was concentrated under reduced pressure and to the residue obtained was added t-butyl methyl ether and water to separate the aqueous layer. After that, the organic layer was again washed with a 1 M aqueous solution of hydrochloric acid, and the aqueous layers were combined. To the mixture was added a saturated aqueous solution of potassium carbonate to make it alkaline, and extracted with t-butyl methyl ether. The aqueous phase was extracted again with t-butyl methyl ether, and the organic layers were combined, dried over magnesium sulfate, filtered and concentrated under reduced pressure to obtain 3-(3,5-dichloro-2,4-difluorophenyl)-3-(trifluoromethyl)pyrrolidine (1.3 g).

$^1$H-NMR (CDCl$_3$) δ: 1.85 (1H, br s), 2.25-2.34 (1H, m), 2.60-2.69 (1H, m), 2.96-3.09 (1H, m), 3.16-3.31 (2H, m), 3.94 (1H, dd), 7.29 (1H, t).

1,3-Dichloro-2,4-difluoro-5-(3,3,3-trifluoroprop-1-en-2-yl)benzene can be also synthesized via 1-(3,5-dichloro-2,4- difluorophenyl)-2,2,2-trifluoroethanone from 1,3-dichloro-2,4-difluoro-5-iodobenzene as shown below.

Step 1

Synthesis of 1-(3,5-dichloro-2,4-difluorophenyl)-2,2,2-trifluoroethanone

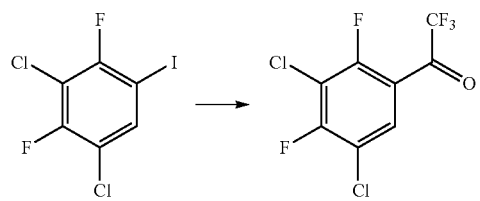 [SMILES: Fc1c(Cl)cc(I)c(F)c1Cl ; O=C(c1cc(Cl)c(F)c(Cl)c1F)C(F)(F)F]

1,3-Dichloro-2,4-difluoro-5-iodobenzene (4.0 g) was dissolved in tetrahydrofuran and cooled to −10 degree. A 2.0 M solution of isopropylmagnesium chloride in tetrahydrofuran (10 ml) was added dropwise via a dropping funnel. The reaction mixture was stirred for 1 hour at same temperature. A solution of ethyl trifluoroacetate (2.76 g) in tetrahydrofuran (6 ml) was added dropwise and the reaction mixture was allowed to warm to ambient temperature. The reaction mixture was diluted with t-butyl methyl ether and washed with 1 N NaOH and then brine. The combined extracts were dried over magnesium sulfate. After filtered off, the filtrate was concentrated in vacuo to give crude product which was purified with Kugel-Rohr to give 1-(3,5-dichloro-2,4-difluorophenyl)-2,2,2-trifluoroethanone (2.5 g).

$^1$H-NMR (CDCl$_3$) δ: 7.90 (t)

Step 2

Synthesis of 1,3-dichloro-2,4-difluoro-5-(3,3,3-trifluoroprop-1-en-2-yl)benzene

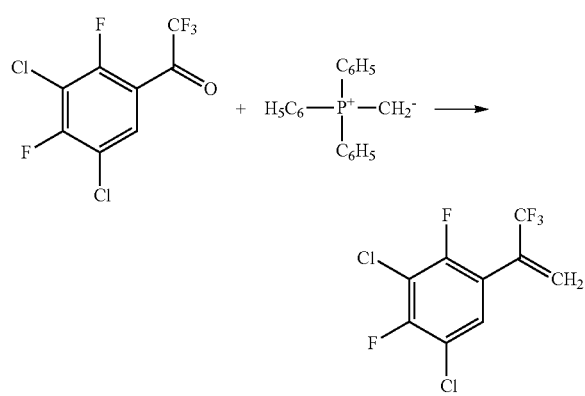

To the suspension of methyl triphenylphosphonium iodide (1.92 g) in tetrahydrofuran (12 ml) was added potassium tert-butoxide (0.53 g) slowly at argon atmosphere below 0° C. on ice/water bath. The reaction mixture turned to yellow and was stirred for 0.5 h. To the mixture was added a solution of 1-(3,5-dichloro-2,4-difluorophenyl)-2,2,2-trifluoroethanone (1.15 g) in tetrahydrofuran (3 ml) dropwise on ice/water bath. After addition, the reaction mixture was warmed to room temperature and stirred over night. The reaction mixture was diluted with pentane and water. The organic phase was separated and washed with water and dried over MgSO4. The crude residue was purified on silica-gel column chromatography (eluent: n-hexane) to give 1,3-dichloro-2,4-difluoro-5-(3,3,3-trifluoroprop-1-en-2-yl)benzene (0.80 g).

$^1$H-NMR (CDCl$_3$) δ: 7.32 (1H, t), 6.26 (1H, s), 5.80 (1H, s)

TABLE 3

Further intermediates of formula (Int-1)

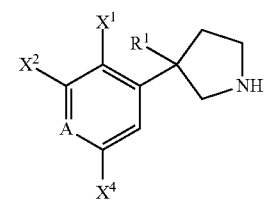

(Int-1)

| No | X$^1$ | X$^2$ | A | X$^4$ | R$^1$ | cf. |
|---|---|---|---|---|---|---|
| Int-1-1 | F | Cl | C—H | Cl | CF$_3$ | Preparation examples |
| Int-1-2 | H | CF$_3$ | N | CF$_3$ | CF$_3$ | Preparation examples |
| Int-1-3 | F | Cl | F | Cl | CF$_3$ | Preparation examples |
| Int-1-4 | H | Cl | C—H | Cl | CF$_3$ | WO 2008/128711 |
| Int-1-5 | H | Br | C—H | Br | CF$_3$ | WO 2008/128711 |
| Int-1-6 | H | CF$_3$ | C—H | CF$_3$ | CF$_3$ | WO 2008/128711 |
| Int-1-7 | H | Cl | C—Cl | Cl | CF$_3$ | WO 2008/128711 |
| Int-1-8 | H | Cl | C—Cl | CF$_3$ | CF$_3$ | WO 2008/128711 |
| Int-1-9 | H | CH$_3$ | C—NO$_2$ | CH$_3$ | CF$_3$ | WO 2008/128711 |
| Int-1-10 | Cl | H | C—Cl | H | CF$_3$ | WO 2008/128711 |
| Int-1-11 | Cl | Cl | C—H | H | CF$_3$ | WO 2008/128711 |
| Int-1-12 | H | Cl | C—Cl | H | CF$_3$ | WO 2008/128711 |
| Int-1-13 | H | Cl | C—H | H | CF$_3$ | WO 2008/128711 |
| Int-1-14 | H | Br | C—H | H | CF$_3$ | WO 2008/128711 |
| Int-1-15 | H | NO$_2$ | C—H | H | CF$_3$ | WO 2008/128711 |
| Int-1-16 | H | CN | C—H | H | CF$_3$ | WO 2008/128711 |
| Int-1-17 | H | CF$_3$ | C—H | H | CF$_3$ | WO 2008/128711 |
| Int-1-18 | H | OCF$_3$ | C—H | H | CF$_3$ | WO 2008/128711 |
| Int-1-19 | H | SCF$_3$ | C—H | H | CF$_3$ | WO 2008/128711 |
| Int-1-20 | H | S(O)CF$_3$ | C—H | H | CF$_3$ | WO 2008/128711 |
| Int-1-21 | H | SO$_2$CF$_3$ | C—H | H | CF$_3$ | WO 2008/128711 |
| Int-1-22 | H | Cl | C—H | Br | CF$_3$ | WO 2008/128711 |
| Int-1-23 | F | Cl | C—H | H | CF$_3$ | WO 2008/128711 |
| Int-1-24 | F | CF$_3$ | C—H | H | CF$_3$ | WO 2008/128711 |
| Int-1-25 | F | H | C—H | Cl | CF$_3$ | WO 2008/128711 |
| Int-1-26 | F | Cl | C—H | CF$_3$ | CF$_3$ | WO 2008/128711 |
| Int-1-27 | H | CF$_3$ | C—F | H | CF$_3$ | WO 2008/128711 |
| Int-1-28 | H | Cl | C—F | Cl | CF$_3$ | WO 2008/128711 |
| Int-1-29 | H | Cl | C—Br | Cl | CF$_3$ | WO 2008/128711 |
| Int-1-30 | H | Cl | C—Cl | Br | CF$_3$ | WO 2008/128711 |
| Int-1-31 | H | F | C—H | F | CF$_3$ | JP 2008/110971 |
| Int-1-32 | H | CF$_3$ | C—H | Cl | CF$_3$ | JP 2011/136928 |

Measurement of log P values was performed according EEC directive 79/831 Annex V.A8 by HPLC (High Performance Liquid Chromatography) on reversed phase columns at pH 2.7 with 0.1% formic acid in water and with acetonitrile (contains 0.1% formic acid) as eluent with a linear gradient from 10% acetonitrle to 95% acetonitrile. Calibration was done with not branched alkan2-ones (with 3 to 16 carbon atoms) with known log P-values (measurement of log P values using retention times with linear interpolation between successive alkanones) Lambda-max-values were determined using UV-spectra from 200 nm to 400 nm and the peak values of the chromatographic signals.

The compounds according to the invention can be formulated in a known manner, as for example given in the below preparation methods without restricting the present invention to the examples.

Preparation Method 1 (Granules)

To a mixture containing 10 parts of the compound of the present invention, 30 parts of bentonite (montmorillonite), 58 parts of talc and 2 parts of lignin sulfonate is added 25 parts of water, and the mixture was well kneaded and granulated with 10 to 40 meshes by an extruding granulator and dried at 40 to 50° C. to obtain granules.

Preparation Method 2 (Granules)

95 parts of clay mineral granules having particle diameter distribution within the range of 0.2 to 2 mm are put into a rotary mixer, and then wetted evenly by spraying of 5 parts of the compound of the present invention together with a liquid diluent under rotating condition and dried at 40 to 50° C. to obtain granules.

Preparation Method 3 (Emulsion)

30 parts of the compound of the present invention, 55 parts of xylene, 8 parts of polyoxyethylene alkyl phenyl ether and 7 parts of calcium alkylbenzenesulfonate are mixed together to obtain the emulsion.

Preparation Method 4 (Wettable Agent)

15 parts of the compound of the present invention, 80 parts of a mixture of white carbon (hydrated amorphous silicon oxide fine powder) and powdered clay (1:5), formalin condensate of 2 parts of sodium alkylbenzenesulfonate and 3 parts of sodium alkylnaphthalenesulfonate is mixed together and the mixture is crushed to obtain a wettable agent.

Preparation Method 5 (Wettable Granules)

20 parts of the active compound of the present invention, 30 parts of lignin sodium sulfonate, 15 parts of bentonite and 35 parts of calcined diatomaceous earth powder are well mixed, and after addition of water, the mixture is then extruded with a screen of 0.3 mm and dried to obtain wettable granules.

As mentioned herein, the compounds according to the invention can be used as actives (active ingredients) for combating/controlling unwanted pests (such as e.g. unwanted insects, acari, helminthes and nematodes). The invention is in particular focussed on combating/controlling pests which occur in agriculture, and in the non-agricultural field such as horticulture, greens and ornamentals and in the veterinary field, which is demonstrated through the following examples without restricting the invention to the examples.

BIOLOGICAL EXAMPLES

*Boophilus microplus*

Injectiontest

Solvent: dimethyl sulfoxide

To produce a suitable preparation of active compound, 10 mg of active compound are dissolved in 0.5 ml solvent, and the concentrate is diluted with solvent to the desired concentration.

Five adult engorged female ticks (*Boophilus microplus*) are injected with 1 μl compound solution into the abdomen. Ticks are transferred into replica plates and incubated in a climate chamber.

After 7 days, the egg deposition of fertile eggs is monitored. Eggs where fertility is not visible are stored in glass tubes in a climate chamber till hatching after about 42 days. An efficacy of 100% means that all eggs are infertile; 0% means that all eggs are fertile.

In this test, for example, the following compounds from the preparation examples showed good activity of 100% at an application rate of 20 μg/animal: I-A-1, I-A-2, I-A-13, I-A-18, I-A-21, I-A-31, I-A-33, I-A-37, I-A-79, I-A-40, I-A-115

*Ctenocephalides felis*—Oral Test

Solvent: dimethyl sulfoxide

To produce a suitable preparation of active compound, 10 mg of active compound are dissolved in 0.5 ml solvent, and the concentrate is diluted with cattle blood to the desired concentration.

Approximately 20 adult unfed cat fleas (*Ctenocephalides felis*) are placed in flea chambers. The blood chamber, sealed with parafilm on the bottom, are filled with cattle blood supplied with compound solution and placed on the gauze covered top of the flea chamber, so that the fleas are able to suck the blood. The blood chamber is heated to 37° C. whereas the flea chamber is kept at room temperature.

After 2 days mortality in % is determined 100% means that all the fleas have been killed; 0% means that none of the fleas have been killed.

In this test, for example, the following compounds from the preparation examples showed good activity of 100% at an application rate of 100 ppm: I-A-1, I-A-2, I-A-13, I-A-18, I-A-21, I-A-31, I-A-33, I-A-37, I-A-40, I-A-79

In this test, for example, the following compounds from the preparation examples showed good activity of 95% at an application rate of 100 ppm: I-A-115

*Lucilia cuprina*—Test solvent: dimethyl sulfoxide 10 mg active compound are dissolved in 0.5 ml Dimethylsulfoxid. Serial dilutions are made to obtain the desired rates.

Approximately 20 1$^{st}$ instar larvae of the Australian sheep blowfly (*Lucilia cuprina*) are transferred into a test tube containing minced horse meat and compound solution of the desired concentration.

After 2 days mortality in % is determined. 100% means that all the larvae have been killed; 0% means that none of the larvae have been killed.

In this test, for example, the following compounds from the preparation examples showed good activity of 100% at an application rate of 100 ppm: I-A-1, I-A-2, I-A-13, I-A-18, I-A-21, I-A-31, I-A-33, I-A-37, I-A-40, I-A-79, I-A-115

*Musca domestica*—Test

Solvent: dimethyl sulfoxide

To produce a suitable preparation of active compound, 10 mg of active compound are dissolved in 0.5 ml solvent, and the concentrate is diluted with water to the desired concentration.

10 adult house flies (*Musca domestica*) are transferred into a container, containing a sponge soaked with a mixture of sugar solution and compound solution of the desired concentration.

After 2 days mortality in % is determined. 100% means that all the flies have been killed; 0% means that none of the flies have been killed.

In this test, for example, the following compounds from the preparation examples showed good activity of 100% at an application rate of 100 ppm: I-A-33, I-A-37

In this test, for example, the following compounds from the preparation examples showed good activity of 90% at an application rate of 100 ppm: I-A-13

In this test, for example, the following compounds from the preparation examples showed goo, activity of 80% at an application rate of 100 ppm: I-A-2, I-A-31

*Myzus persicae*—Spray Test
Solvent: 78.0 parts by weight acetone
  1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinensis*) leaf disks infected with all instars of the green peach aphid (*Myzus persicae*), are sprayed with a preparation of the active ingredient of the desired concentration.

After 6 days, mortality in % is determined 100% means that all aphids have been killed; 0% means that none of the aphids have been killed.

In this test, for example, the following compounds from the preparation examples showed good activity of 100% at an application rate of 100 g/ha: I-A-4, I-A-13, I-A-14, I-A-19, I-A-26, I-A-31, I-A-38

In this test, for example, the following compounds from the preparation examples showed good activity of 90% at an application rate of 100 g/ha: I-A-6, I-A-16, I-A-37, I-A-42, I-A-79

In this test, for example, the following compounds from the preparation examples showed good activity of 80% at an application rate of 100 g/ha: I-A-9

*Phaedon cochleariae*—Spray Test
Solvent: 78.0 parts by weight of acetone
  1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinensis*) leaf-disks are sprayed with a preparation of the active ingredient of the desired concentration. Once dry, the leaf disks are infested with mustard beetle larvae (*Phaedon cochleariae*).

After 7 days mortality in % is determined. 100% means that all beetle larvae have been killed and 0% means that none of the beetle larvae have been killed.

In this test, for example, the following compounds from the preparation examples showed good activity of 100% at an application rate of 100 g/ha: I-A-1, I-A-4, I-A-6, I-A-9, I-A-13, I-A-14, I-A-16, I-A-18, I-A-19, I-A-21, I-A-26, I-A-31, I-A-33, I-A-37, I-A-38, I-A-40, I-A-42, I-A-43, I-A-45, I-A-79, I-A-115, I-A-127, I-A-139, I-B-115

*Spodoptera frugiperda*—Spray Test
Solvent: 78.0 parts by weight acetone
  1.5 parts by weight dimethylformamide
Emulsifier: 0.5 parts by weight alkylarylpolyglycolether To produce a suitable preparation of the active compound, 1 part by weight of active compound is mixed with the stated amount of solvent and emulsifier, and the concentrate is diluted with emulsifier-containing water to the desired concentration.

Maize (*Zea mays*) leaf sections are sprayed with a preparation of the active ingredient of the desired concentration. Once dry, the leaf sections are infested with fall armyworm larvae (*Spodoptera frugiperda*).

After 7 days, mortality in % is determined 100% means that all caterpillars have been killed and 0% means that none of the caterpillars have been killed.

In this test, for example, the following compounds from the preparation examples showed good activity of 100% at an application rate of 100 g/ha: I-A-1, I-A-4, I-A-6, I-A-9, I-A-13, I-A-14, I-A-16, I-A-18, I-A-19, I-A-21, I-A-26, I-A-31, I-A-33, I-A-37, I-A-38, I-A-42, I-A-43, I-A-45, I-A-79, I-A-115, I-A-127, I-A-139

In this test, for example, the following compounds from the preparation examples showed good activity of 83% at an application rate of 100 g/ha: I-A-40, I-B-115

*Tetranychus urticae*—Spray Test, OP-Resistant
Solvent: 78.0 parts by weight acetone
  1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration.

French beans (*Phaseolus vulgaris*) which are heavily infested with all stages of the two spotted spidermite (*Tetranychus urticae*), are sprayed with a preparation of the active ingredient of the desired concentration.

After 6 days, mortality in % is determined. 100% means that all spider mites have been killed and 0% means that none of the spider mites have been killed.

In this test, for example, the following compounds from the preparation examples showed good activity of 100% at an application rate of 100 g/ha: I-A-1, I-A-4, I-A-6, I-A-9, I-A-13, I-A-14, I-A-16, I-A-18, I-A-21, I-A-26, I-A-31, I-A-33, I-A-37, I-A-42, I-A-45, I-A-79

In this test, for example, the following compounds from the preparation examples showed good activity of 90% at an application rate of 100 g/ha: I-A-19, I-A-38, I-A-40, I-A-43, I-A-127, I-B-115

The invention claimed is:
1. Compound of formula (I):

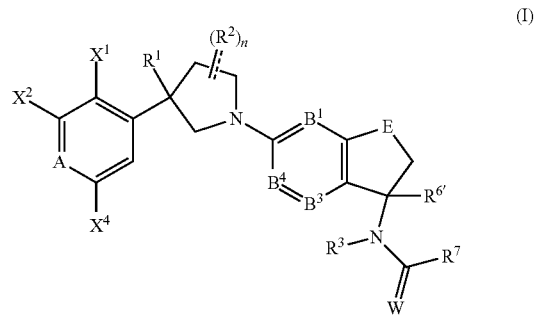

wherein
R$^1$ is C$_{1-12}$ alkyl, C$_{3-8}$ cycloalkyl, C$_{1-12}$ haloalkyl, C$_{3-8}$ halocycloalkyl;
R$^2$ is oxo and/or thioxo and n is 1 or 2, if the dotted line in formula (I) stands for a bond, so that R$^2$ is bound through a double bond to the pyrrolidine ring; or
R$^2$ independently is halogen, nitro, cyano, hydroxy, mercapto, amino, C$_{1-12}$ alkyl, C$_{1-12}$ haloalkyl, C$_{1-12}$ alkoxy, C$_{1-12}$ haloalkoxy, C$_{1-12}$ alkylsulfenyl, C$_{1-12}$ alkylsulfinyl, C$_{1-12}$ alkylsulfonyl, C$_{1-12}$ haloalkylsulfenyl, C$_{1-12}$ haloalkylsulfinyl, $C_{1-12}$ haloalkylsulfonyl, sulfur pentafluoride, $C_{1-12}$ alkoxy-carbonyl, $C_{1-12}$ haloalkoxy-carbonyl, $C_{1-12}$ alkoxy-carbonyloxy or $C_{1-12}$ haloalkoxy-carbonyloxy, n is 1 or 2, if the dotted line in formula (I) has no meaning, so that $R^2$ is bound through a single bond to the pyrrolidine ring;

A is $C-X^3$ or nitrogen;

$X^1$, $X^2$, $X^3$ and $X^4$ each independently are hydrogen, halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino or sulfur pentafluoride;

$B^1$ is $C-Y^1$ or nitrogen;
$B^3$ is $C-Y^3$ or nitrogen;
$B^4$ is $C-Y^4$ or nitrogen;

$Y^1$, $Y^3$ and $Y^4$ each independently are hydrogen, halogen, nitro, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino, sulfur pentafluoride, aryl or heterocyclyl;

$R^3$ is hydrogen, cyano, hydroxy, mercapto, amino, $C_{1-12}$ alkyl, $C_{1-12}$ haloalkyl, $C_{2-12}$ alkenyl, $C_{2-12}$ haloalkenyl, $C_{2-12}$ alkynyl, $C_{2-12}$ haloalkynyl, $C_{1-12}$ alkyl-carbonyl, $C_{1-12}$ haloalkyl-carbonyl, $C_{1-12}$ alkoxy-carbonyl or $C_{1-12}$ haloalkoxy-carbonyl, $C_{1-12}$ alkoxy-$C_{1-12}$ alkyl, or cyano-$C_{1-12}$ alkyl;

$R^{6'}$ is hydrogen or $C_1$-$C_6$ alkyl, $R^7$ is hydrogen, or optionally substituted $C_{1-12}$ alkyl, $C_{1-12}$ cyanoalkyl, and $C_{1-12}$ haloalkyl, optionally substituted $C_{3-8}$ cycloalkyl, $C_{3-8}$ halocycloalkyl, $C_{3-8}$ cycloalkyl-$C_{1-12}$ alkyl, and $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, amino, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino, optionally substituted aryl and aryl-$C_{1-12}$ alkyl, a optionally substituted heterocyclic group, $C_{1-12}$ alkyl substituted with a heterocyclic group, $C_{1-12}$alkylcarbonyl, $C_{1-12}$haloalkylcarbonyl or $(R^8)(R^9)N-CO-$;

$R^8$ and $R^9$ each independently are hydrogen, cyano, hydroxy, amino, $C_{1-12}$ alkyl, $C_{1-12}$ haloalkyl, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$alkoxy, $C_{1-12}$haloalkoxy, $C_{1-12}$alkoxy-$C_{1-12}$alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl-S(O)—$C_{1-12}$ alkyl, $C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, $C_{1-12}$ alkylsulfonyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino, cyano $C_{1-12}$ alkyl, cyano-$C_{3-8}$ cycloalkyl, aryl, aryl-$C_{1-12}$ alkyl, a heterocyclic group or $C_{1-12}$ alkyl substituted with a heterocyclic group;

W is oxygen or sulfur;

E is oxygen, sulfur or a $C_{1-3}$ alkandiyl-group which group can be optionally substituted by 1 or 2 $C_1$-$C_6$ alkyl groups.

2. Compound according to claim 1, wherein
$R^1$ is $CF_3$;
$R^2$ is hydroxy;
n is 1;
$B^1$ is $C-Y^1$;
$B^3$ is $C-Y^3$;
$B^4$ is $C-Y^4$; and
E is oxygen or a $C_{1-3}$ alkandiyl-group which group can be optionally substituted by 1 or 2 $C_1$-$C_6$ alkyl groups.

3. Compound according to claim 1, wherein
$R^1$ is $CF_3$;
$R^2$ is hydroxy;
n is 1;
$B^1$ is nitrogen;
$B^3$ is $C-Y^3$;
$B^4$ is $C-Y^4$; and
E is oxygen or a $C_{1-3}$ alkandiyl-group which group can be optionally substituted by 1 or 2 $C_1$-$C_6$ alkyl groups.

4. Compound according to claim 1, wherein
$R^1$ is $CF_3$;
$R^2$ is hydroxy;
n is 1;
$B^1$ is $C-Y^1$;
$B^3$ is nitrogen;
$B^4$ is $C-Y^4$; and
E is oxygen or a $C_{1-3}$ alkandiyl-group which group can be optionally substituted by 1 or 2 $C_1$-$C_6$ alkyl groups.

5. Compound according to claim 1, wherein
$R^1$ is $CF_3$;
$R^2$ is hydroxy;
n is 1;
$B^1$ is $C-Y^1$;
$B^3$ is $C-Y^3$;
$B^4$ is nitrogen; and
E is oxygen or a $C_{1-3}$ alkandiyl-group which group can be optionally substituted by 1 or 2 $C_1$-$C_6$ alkyl groups.

6. Compound according to claim 1, wherein
$R^1$ is $CF_3$;
$R^2$ is an oxo group;
n is 1;
$B^1$ is $C-Y^1$;
$B^3$ is $C-Y^3$;
$B^4$ is $C-Y^4$; and
E is oxygen or a $C_{1-3}$ alkandiyl-group which group can be optionally substituted by 1 or 2 $C_1$-$C_6$ alkyl groups.

7. Compound according to claim 1, wherein
$R^1$ is $CF_3$;
$R^2$ is an oxo group;
n is 1;
$B^1$ is nitrogen;
$B^3$ is $C-Y^3$;
$B^4$ is $C-Y^4$; and
E is oxygen or a $C_{1-3}$ alkandiyl-group which group can be optionally substituted by 1 or 2 $C_1$-$C_6$ alkyl groups.

8. Method for preparation of one or more compounds as defined in claim 1 comprising oxidation of a compound of formula (II)

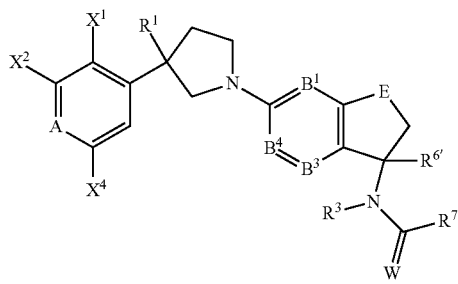

(II)

wherein
R¹ is $C_{1-12}$; alkyl $C_{3-8}$ cycloalkyl, $C_{1-12}$ haloalkyl, $C_{3-8}$ halocycloalkyl;

A is C—X³ or nitrogen;

X¹, X², X³ and X⁴ each independently are hydrogen, halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino or sulfur pentafluoride;

B¹ is C—Y¹ or nitrogen;
B³ is C—Y³ or nitrogen;
B⁴ is C—Y⁴ or nitrogen;

Y¹, Y³ and Y⁴ each independently are hydrogen, halogen, nitro, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{1-12}$, alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino, sulfur pentafluoride, aryl or heterocyclyl;

R³ is hydrogen, cyano, hydroxy, mercapto, amino, $C_{1-12}$ alkyl, $C_{1-12}$ haloalkyl, $C_{2-12}$ alkenyl, $C_{2-12}$ haloalkenyl, $C_{2-12}$ alkynyl, $C_{2-12}$ haloalkynyl, $C_{1-12}$ alkyl-carbonyl, $C_{1-12}$ haloalkyl-carbonyl, $C_{1-12}$ alkoxycarbonyl or $C_{1-12}$ haloalkoxy-carbonyl, $C_{1-12}$ alkoxy-$C_{1-12}$ alkyl, or cyano $C_{1-12}$ alkyl;

R⁶ is hydrogen or $C_1$-$C_6$ alkyl,

R⁷ is hydrogen, or optionally substituted $C_{1-12}$ alkyl, $C_{1-12}$ cyanoalkyl, and $C_{1-12}$ haloalkyl, optionally substituted $C_{3-8}$ cycloalkyl, $C_{3-8}$ halocycloalkyl, $C_{3-8}$ cycloalkyl-$C_{1-12}$ alkyl, and $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)₂—$C_{1-12}$ alkyl, $C_{1-12}$ haloalkyl-S(O)₂—$C_{1-12}$ alkyl, amino, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino, optionally substituted aryl and aryl-$C_{1-12}$ alkyl, a optionally substituted heterocyclic group, $C_{1-12}$ alkyl substituted with a heterocyclic group, $C_{1-12}$ alkylcarbonyl, $C_{1-12}$ haloalkylcarbonyl or (R⁸)(R⁹)N—CO—;

R⁸ and R⁹ each independently are hydrogen, cyano, hydroxy, amino, $C_{1-12}$ alkyl, $C_{1-12}$ haloalkyl, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)₂—$C_{1-12}$ alkyl, $C_{1-12}$ haloalkyl-S(O)₂—$C_{1-12}$ alkyl, $C_{1-12}$ alkylsulfonyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino, cyano $C_{1-12}$ alkyl, cyano-$C_{3-8}$ cycloalkyl, aryl, aryl-$C_{1-12}$ alkyl, a heterocyclic group or $C_{1-12}$ alkyl substituted with a heterocyclic group;

W is oxygen or sulfur;

E is oxygen, sulfur or a $C_{1-3}$ alkandiyl-group which group can be optionally substituted by 1 or 2 $C_1$-$C_6$ alkyl groups, optionally in the presence of a catalyst.

9. Method according to claim 8, wherein the oxidation agent is at least one of $H_2O_2$, $MnO_2$, $KMnO_4$, $RuO_4$, m-chloroperbenzoic acid, 2,3-dichloro-5,6-dicyano-1,4-benzoquinone, tetrachloro-1,2-benzoquinone, tetrachloro-1,4-benzoquinone, ceric(IV)ammonium nitrate, or silver(II)salts, silver(II)fluoride, bis(α,α'-bipyridine)silver(II)nitrate, bis(α,α'-bipyridine)silver(II)peroxydisulfate, silver(II)picolinate, and tetrakis(pyridine)silver(II), [bis(trifluoroacetoxy)iodo]benzene, [bis(acetoxy)iodo]benzene, iodosobenzene, 2-iodoxybenzoic acid, pentafluoroiodosobenzene, or air (oxygen).

10. Method according to claim 8, wherein the catalyst is one or more of a transition metal catalyst, an acid catalyst, or a phase transfer catalyst.

11. A compound according to claim 1 capable of being used for controlling one or more of insects, arachnids, helminths, nematodes and molluscs, which are encountered in agriculture, in horticulture, in animal husbandry, in forests, in gardens and leisure facilities, in protection of stored products and of materials, and/or in hygiene sector.

12. A compound according to claim 1 capable of being used as a plant protection agent and/or for treating seeds.

13. A method of controlling unwanted pests comprising allowing a compound of formula (I) as claimed in claim 1 to act on one or more of insects, arachnids, helminths, nematodes and molluscs, which are encountered in agriculture, in horticulture, in animal husbandry, in forests, in gardens and leisure facilities, in protection of stored products and of materials, and/or in hygiene sector.

\* \* \* \* \*